United States Patent
Takahashi

(10) Patent No.: US 12,032,104 B2
(45) Date of Patent: Jul. 9, 2024

(54) ULTRASONIC DIAGNOSTIC APPARATUS AND METHOD OF DETERMINING SCANNING CONDITION

(71) Applicant: Canon Medical Systems Corporation, Otawara (JP)

(72) Inventor: Hiroki Takahashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 79 days.

(21) Appl. No.: 17/447,588

(22) Filed: Sep. 14, 2021

(65) Prior Publication Data

US 2022/0079564 A1 Mar. 17, 2022

(30) Foreign Application Priority Data

Sep. 14, 2020 (JP) ................. 2020-154015

(51) Int. Cl.
| | | |
|---|---|---|
| G01S 7/00 | (2006.01) | |
| G01S 7/52 | (2006.01) | |
| G01S 15/89 | (2006.01) | |
| A61B 8/00 | (2006.01) | |
| A61B 8/06 | (2006.01) | |
| A61B 8/08 | (2006.01) | |

(52) U.S. Cl.
CPC ...... *G01S 7/52085* (2013.01); *G01S 15/8915* (2013.01); *G01S 15/8979* (2013.01); *G01S 15/8997* (2013.01); *A61B 8/06* (2013.01); *A61B 8/469* (2013.01); *A61B 8/488* (2013.01); *A61B 8/5207* (2013.01); *G01S 7/52042* (2013.01)

(58) Field of Classification Search
CPC ............ G01S 7/52085; G01S 15/8915; G01S 15/8979; G01S 15/8997; G01S 7/52042; G01S 7/52047; A61B 8/06; A61B 8/469; A61B 8/488; A61B 8/5207; A61B 8/485
See application file for complete search history.

(56) References Cited

U.S. PATENT DOCUMENTS

| | | | |
|---|---|---|---|
| 6,629,929 B1 | 10/2003 | Jago et al. | |
| 10,456,110 B2 | 10/2019 | Takano et al. | |

(Continued)

FOREIGN PATENT DOCUMENTS

| | | | |
|---|---|---|---|
| JP | 2005-013280 A | 1/2005 | |
| JP | 2005-312632 A | 11/2005 | |

(Continued)

OTHER PUBLICATIONS

Extended European Search Report dated Feb. 2, 2022 in European Patent Application No. 21196568.6, 9 pages.

(Continued)

*Primary Examiner* — Pascal M Bui Pho
*Assistant Examiner* — Taylor Deutsch
(74) *Attorney, Agent, or Firm* — Oblon, McClelland, Maier & Neustadt, L.L.P.

(57) ABSTRACT

According to one embodiment, an ultrasonic diagnostic apparatus includes processing circuitry. The processing circuitry acquires a parameter relating to a predetermined imaging mode, the parameter including at least information on an instruction for executing transmit aperture synthesis, and determines a scanning condition for executing the transmit aperture synthesis together with step-alternating scan based on the parameter.

17 Claims, 14 Drawing Sheets

(56) References Cited

U.S. PATENT DOCUMENTS

| | | | |
|---|---|---|---|
| 2008/0146920 A1 | 6/2008 | Lin et al. | |
| 2012/0029350 A1* | 2/2012 | Li | A61B 8/06 600/437 |
| 2019/0209133 A1 | 7/2019 | Takahashi et al. | |
| 2020/0033471 A1 | 1/2020 | Kim et al. | |
| 2020/0268355 A1* | 8/2020 | Watanabe | A61B 8/463 |

FOREIGN PATENT DOCUMENTS

| | | |
|---|---|---|
| JP | 2006-505319 A | 2/2006 |
| JP | 2009-201651 A | 9/2009 |
| JP | WP2016/009544 A1 | 1/2016 |
| JP | 2017-140357 | 8/2017 |
| JP | 2019-118715 A | 7/2019 |
| JP | 2020-69301 | 5/2020 |

OTHER PUBLICATIONS

Office Action mailed Feb. 20, 2024 in Japanese Application No. 2020-154015 filed Sep. 14, 2020.

* cited by examiner

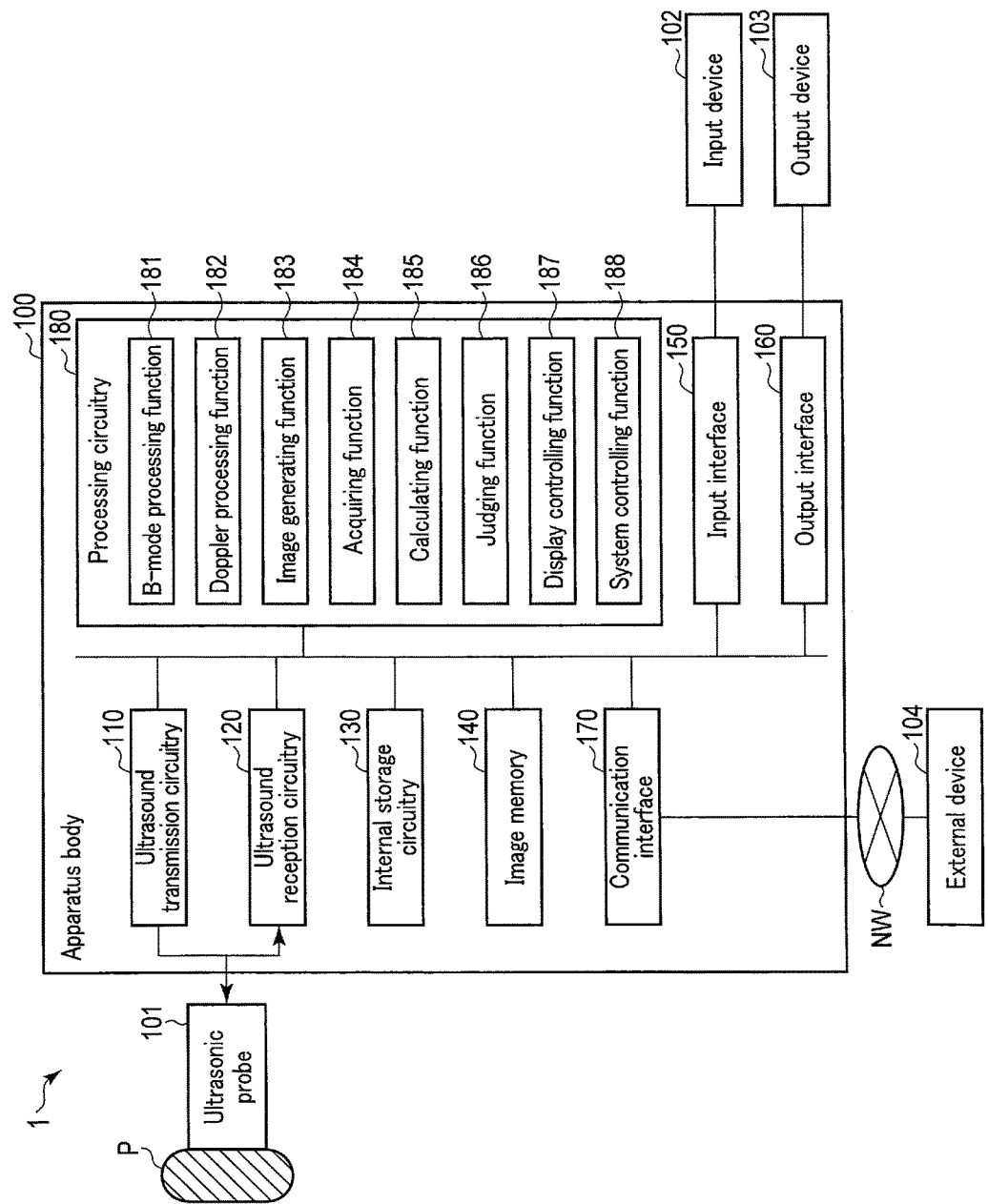
F I G. 1

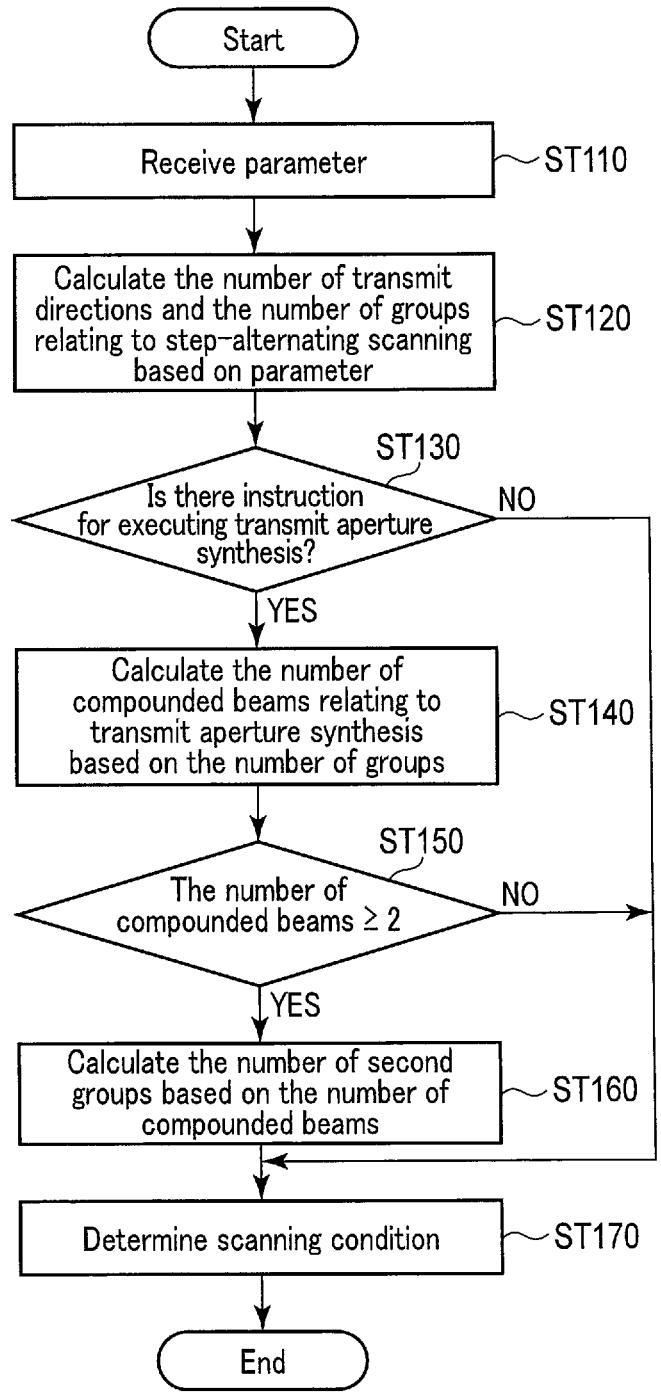
F I G. 2

FIG. 5

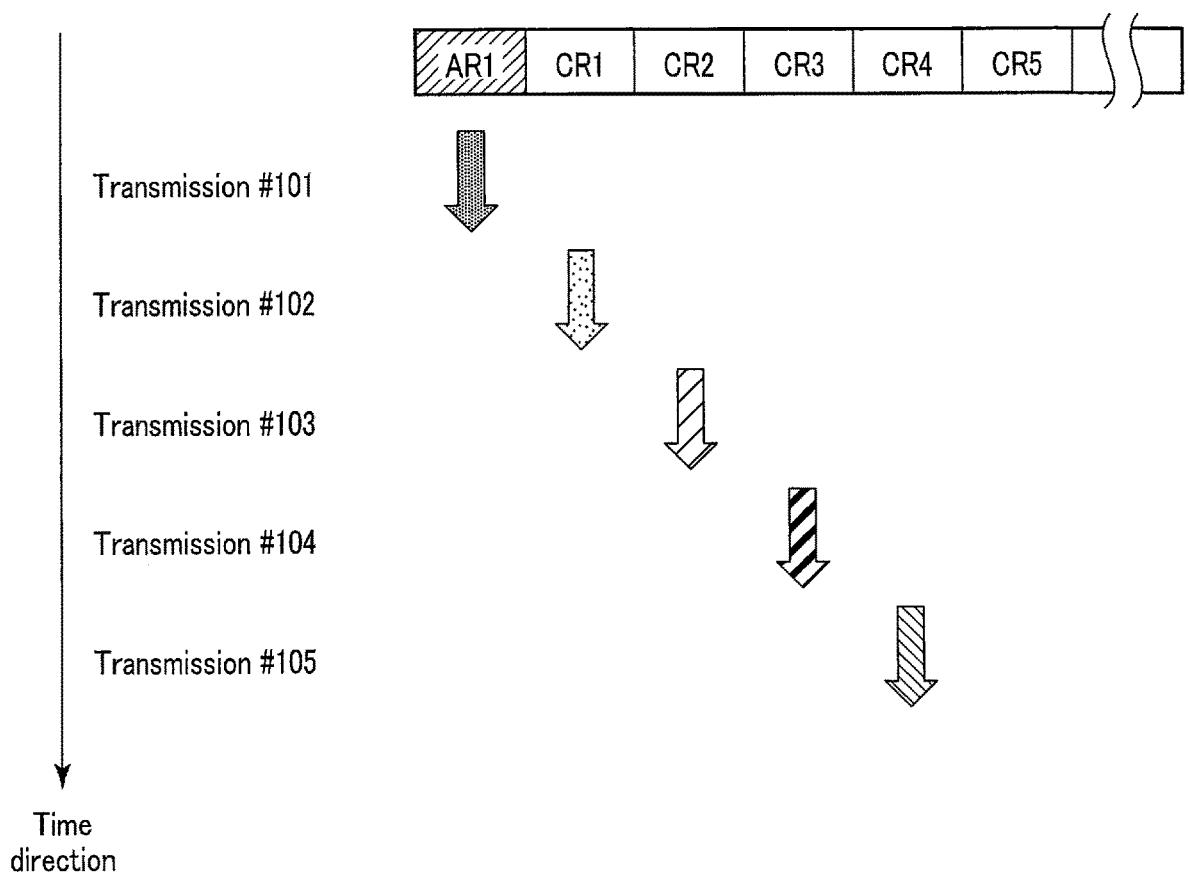
F I G. 7

FIG. 10

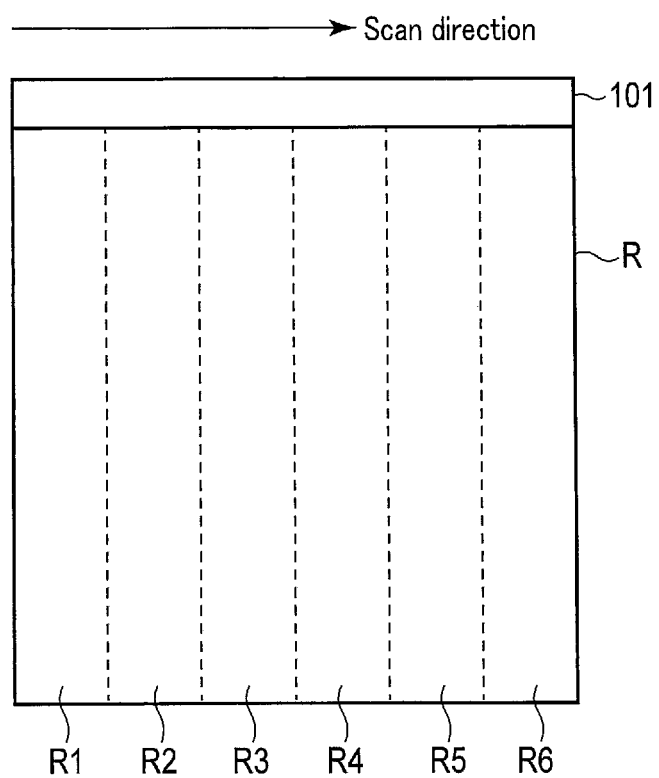
F I G. 15

ULTRASONIC DIAGNOSTIC APPARATUS AND METHOD OF DETERMINING SCANNING CONDITION

CROSS-REFERENCE TO RELATED APPLICATIONS

This application is based upon and claims the benefit of priority from Japanese Patent Application No. 2020-154015, filed Sep. 14, 2020, the entire contents of which are incorporated herein by reference.

FIELD

Embodiments described herein relate generally to an ultrasonic diagnostic apparatus and a method of determining a scanning condition.

BACKGROUND

Conventionally, a Doppler imaging function that estimates and visualizes a displacement amount and a velocity of living tissue such as a blood flow generally uses a transmission/reception control method called step-alternating scan (or packet scanning). The step-alternating scan is a method in which when data strings at the same position are collected, instead of performing transmission and reception continuously at the same beam position, a plurality of beam positions are combined into one set, and transmission and reception are performed at multiple beam positions included in the set sequentially. This makes it possible to lengthen a sampling period without reducing a frame rate and to support measurements of a low-speed blood flow rate.

Moreover, as a method of parallel simultaneous reception in medical ultrasonic diagnosis, there is a technique called transmit aperture synthesis. Transmit aperture synthesis is a method of acquiring multiple reception echo signals whose transmission/reception focal points are formed at the same observation point with transmitted beams having different transmission convergence points, and executing synthesis summation. The use of transmit aperture synthesis allows formation of a high-accuracy transmit beam width that is even in a depth direction in addition to an improvement in S/N and therefore allows generation of ultrasound images with excellent space resolution and contrast resolution.

However, for an ultrasonic diagnostic apparatus, a technique for determining an optimum scanning condition for execution of transmit aperture synthesis together with step-alternating scan has not been known.

BRIEF DESCRIPTION OF THE DRAWINGS

FIG. 1 is a block diagram showing an exemplary configuration of an ultrasonic diagnostic apparatus according to a first embodiment.

FIG. 2 is a flowchart for explaining operations of processing circuitry executing scanning condition determination processing in the first embodiment.

FIG. 5 is a diagram for explaining an ultrasound scanning chart in the first embodiment.

FIG. 7 is a diagram for explaining operations of transmit control through transmit aperture synthesis in the first embodiment.

FIG. 10 is a diagram for explaining an ultrasound scanning chart in an application example of the first embodiment.

FIG. 15 is a diagram for explaining a scan area.

DETAILED DESCRIPTION

Figure 3:
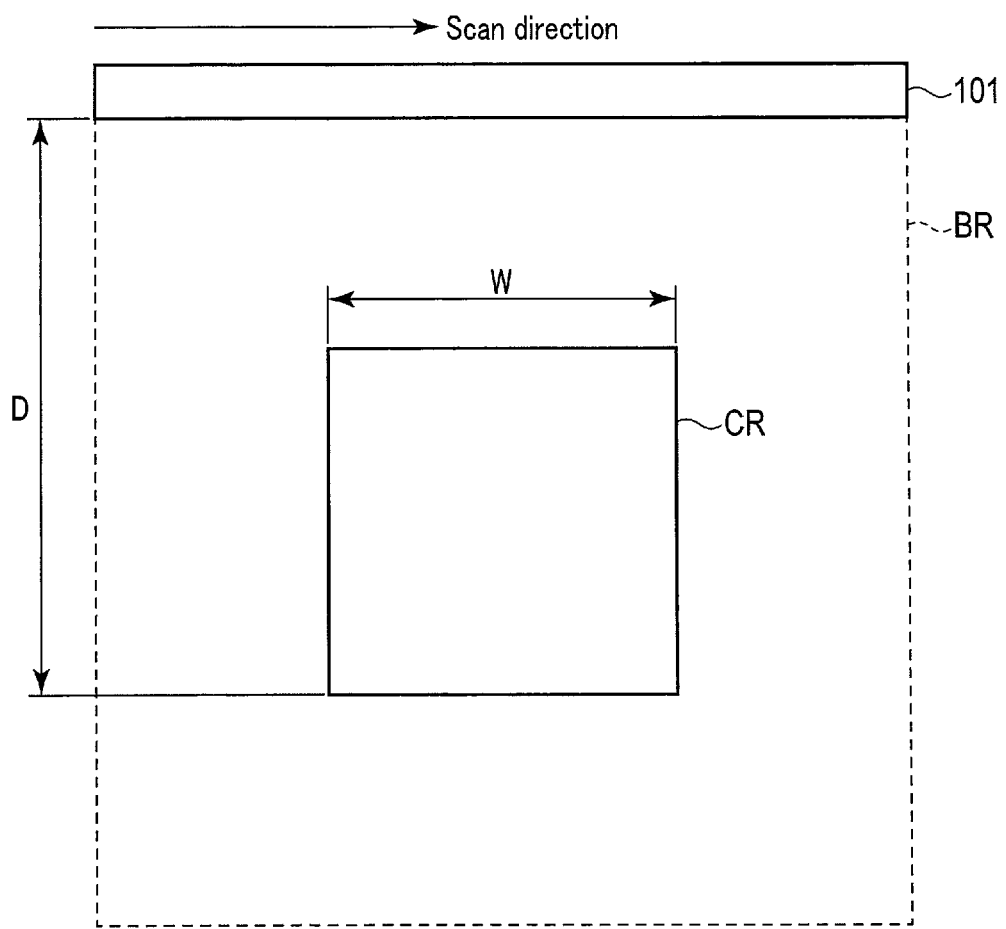
FIG. 3 is a diagram for explaining an entire scan area and a region of interest in the first embodiment.

In general, according to one embodiment, an ultrasonic diagnostic apparatus includes processing circuitry. The processing circuitry acquires a parameter relating to a predetermined imaging mode, the parameter including at least information on an instruction for executing transmit aperture synthesis, and determines a scanning condition for executing the transmit aperture synthesis together with step-alternating scan based on the parameter.

Hereinafter, each embodiment of an ultrasonic diagnostic apparatus will be described with reference to the accompanying drawings.

First Embodiment

FIG. 1 is a block diagram showing an exemplary configuration of an ultrasonic diagnostic apparatus according to the first embodiment. An ultrasonic diagnostic apparatus 1 of FIG. 1 includes an apparatus body 100 and an ultrasonic probe 101. The apparatus body 100 is connected to an input device 102 and the output device 103. The apparatus body 100 is connected to an external device 104 via a network NW. The external device 104 is, for example, a server or the like equipped with a picture archiving and communication system (PACS).

The ultrasonic probe 101 executes ultrasound scanning in a scan area of a living body P, which is a subject, under the control of the apparatus body 100. The ultrasonic probe 101 includes, for example, a plurality of piezoelectric vibrators, a matching layer provided between the piezoelectric vibrators and a case, and a backing material that prevents ultrasonic waves from propagating backwardly against a radiation direction from the piezoelectric vibrators. The ultrasonic probe 101 is, for example, a one-dimensional array linear probe in which a plurality of ultrasonic vibrators are arranged in a predetermined direction. The ultrasonic probe 101 is detachably connected to the apparatus body

100. The ultrasonic probe 101 may be provided with a button pressed for offset processing, freezing an ultrasonic image (freeze action), etc.

The piezoelectric vibrators generate ultrasonic waves based on a drive signal supplied from ultrasound transmission circuitry 110 of the apparatus body 100, which will be described later. In this manner, ultrasonic waves are transmitted from the ultrasonic probe 101 to the living body P. When ultrasonic waves are transmitted from the ultrasonic probe 101 to the living body P, the transmitted ultrasonic waves are sequentially reflected on an acoustic impedance discontinuous surface of the body tissue of the living body P, and are received as reflected wave signals by the piezoelectric vibrators. Amplitudes of the received reflected wave signals depend on the difference in acoustic impedance on the discontinuous surface from which the ultrasound waves are reflected. When a transmitted ultrasonic pulse is reflected by a moving blood flow, a surface of a cardiac wall or the like, a frequency of the reflected wave signal is shifted, due to the Doppler effect, depending on a velocity component of a moving object in an ultrasonic transmission direction. The ultrasonic probe 101 receives the reflected wave signals from the living body P, and converts them into electric signals.

FIG. 1 shows an example of a connection relationship between the ultrasonic probe 101 as a single unit and the apparatus body 100. A plurality of ultrasonic probes may be connected to the apparatus body 100. Which of the connected ultrasonic probes is to be used for ultrasound scanning can be discretionarily selected, for example, with a software button on a touch panel described later.

The apparatus body 100 generates an ultrasonic image based on reflected wave signals received by the ultrasonic probe 101. The apparatus body 100 includes ultrasound transmission circuitry 110, ultrasound reception circuitry 120, internal storage circuitry 130, an image memory 140, an input interface 150, an output interface 160, a communication interface 170, and processing circuitry 180.

The ultrasound transmission circuitry 110 is a processor that supplies a drive signal to the ultrasonic probe 101. The ultrasound transmission circuitry 110 is implemented by, for example, trigger generation circuitry, delay circuitry, pulser circuitry, etc. The trigger generation circuitry repeatedly generates a rate pulse for forming a transmission ultrasonic wave at a predetermined rate frequency. The delay circuitry provides each rate pulse generated by the trigger generation circuitry with a delay time for each of a plurality of piezoelectric vibrators necessary for converging ultrasonic waves generated by the ultrasonic probe in a beam form and determining transmission directivity. The pulser circuitry applies a drive signal (drive pulse) to the ultrasonic vibrators provided in the ultrasonic probe 101 at a timing based on the rate pulse. By varying the delay time provided to each rate pulse by the delay circuitry, the transmission direction from the piezoelectric vibrator surfaces can be freely adjusted.

The ultrasound transmission circuitry 110 can discretionarily change an output intensity of ultrasound waves by the drive signal. With an increased output intensity, the ultrasonic diagnostic apparatus can suppress influence of attenuation of ultrasonic waves in the living body P. When the influence of attenuation of ultrasonic waves is reduced, the ultrasonic diagnostic apparatus can acquire reflected wave signals having a large S/N ratio at the time of reception.

In general, an ultrasonic wave propagating in a living body P experiences attenuation of its vibration intensity (which may also be called acoustic power) corresponding to the output intensity. The attenuation of acoustic power occurs due to absorption, scattering, reflection, etc. How much attenuation occurs in the acoustic power depends on the frequency of ultrasonic waves, and the distance in the direction of radiation of ultrasonic waves. For example, a larger frequency of ultrasonic waves produces less attenuation. A longer distance in the direction of ultrasound wave radiation produces larger attenuation.

The ultrasound reception circuitry 120 is a processor that performs various types of processing on reflected wave signals received by the ultrasonic probe 101 to generate reception signals. The ultrasound reception circuitry 120 generates reception signals for the ultrasound reflected wave signals acquired by the ultrasonic probe 101. Specifically, the ultrasound reception circuitry 120 is realized by, for example, a preamplifier, an A/D converter, a demodulator, a beam former, etc. The preamplifier performs gain correction processing for each channel by amplifying the reflected wave signal received by the ultrasonic probe 101. The A/D converter converts the gain-corrected reflected wave signal into a digital signal. The demodulator demodulates the digital signal. The beam former, for example, supplies, to a demodulated digital signal, a delay time required to determine the reception directivity, and adds digital signals to which delay time is supplied. Through addition processing by the beam former, a reception signal is generated in which a reflection component from the direction corresponding to the reception directivity is emphasized.

The internal storage circuitry 130 includes, for example, a magnetic storage medium, an optical storage medium, a processor-readable storage medium such as a semiconductor memory, or the like. The internal storage circuitry 130 stores therein programs for realizing ultrasound transmission and reception, programs relating to scanning condition determination processing described later, various data items, etc. The programs and data may be, for example, pre-stored in the internal storage circuitry 130. The programs and data may be stored and distributed in, for example, a non-transitory storage medium, read from the non-transitory storage medium, and installed in the internal storage circuitry 130. The internal storage circuitry 130 stores B-mode image data, contrast image data, blood flow imaging-related image data, etc., generated by the processing circuitry 180, in response to operational inputs given via the input interface 150. The internal storage circuitry 130 may transfer the stored image data to an external device 104, etc. via the communication interface 170.

The internal storage circuitry 130 may be a drive unit, etc., to read and write various information sets from and to portable storage media such as a CD drive, a DVD drive, and a flash memory. The internal storage circuitry 130 may write the stored data onto a portable storage medium and store the data into an external device 104 via a portable storage medium.

The image memory 140 includes, for example, a magnetic storage medium, an optical storage medium, a processor-readable storage medium such as a semiconductor memory, or the like. The image memory 140 stores therein image data corresponding to a plurality of frames immediately before a freeze operation that is input via the input interface 150. The image data stored in the image memory 140 is, for example, sequentially displayed (cine-displayed).

The internal storage circuitry 130 and the image memory 140 need not necessarily be realized by independent storage devices. The internal storage circuitry 130 and image memory 140 may be realized by a single storage device. The internal storage circuitry 130 and the image memory 140 each may be realized by a plurality of storage devices.

The input interface 150 receives various instructions from an operator via the input device 102. The input device 102 is, for example, a mouse, a keyboard, a panel switch, a slider switch, a trackball, a rotary encoder, an operation panel, or a touch command screen (TCS). The input interface 150 is connected to the processing circuitry 180 via, for example, a bus to convert operational instructions input by an operator into electric signals and output them to the processing circuitry 180. The input interface 150 is not limited to a component that is coupled to a physical operation component such as a mouse and keyboard. Examples of the input interface include a circuit configured to receive an electric signal corresponding to an operation command that is input from an external input device provided separately from the ultrasonic diagnostic apparatus 1 and to output this electric signal to the processing circuitry 180.

The output interface 160 is an interface to output, for example, electric signals from the processing circuitry 180 to the output device 103. The display 103 is any display such as a liquid crystal display, an organic EL display, an LED display, a plasma display, or a CRT display. The output device 103 may be a touch-panel type display serving also as the input device 102. The output device 103 may further include a speaker for sound output, in addition to the display. The output interface 160 is connected to the processing circuitry 180 via, for example, a bus, and outputs an electrical signal from the processing circuitry 180 to the output device 103.

The communication interface 170 is connected to the external device 104 via, for example, the network NW, and performs data communication with the external device 104.

The processing circuitry 180 is, for example, a processor functioning as a center of the ultrasonic diagnostic apparatus 1. The processing circuitry 180 executes a program stored in the internal storage circuitry 130, thereby implementing a function corresponding to the program. The processing circuitry 180 has, for example, a B-mode processing function 181, a Doppler processing function 182, an image generating function 183, an acquiring function 184 (acquisition unit), a calculating function 185 (calculation unit), a judging function 186 (judgment unit), a display controlling function 187 (display controller), and a system controlling function 188 (determination unit).

The B-mode processing function 181 is a function for generating B-mode data based on a reception signal received from the ultrasound reception circuitry 120. With the B-mode processing function 181, the processing circuitry 180 executes envelop detection processing and logarithmic amplification processing on the reception signal received from the ultrasound reception circuitry 120, and generates data (B-mode data) in which the signal intensity is expressed by a degree of brightness. The generated B-mode data is stored in a raw data memory (not shown) as B-mode raw data on a two-dimensional ultrasonic scanning line (raster).

Through the B-mode processing function 181, the processing circuitry 180 can execute a contrast echo method, for example, contrast harmonic imaging (CHI). That is, the processing circuitry 180 can separate reflected wave data of the living body P into which a contrast agent is injected (harmonic components or subharmonic components) and reflected wave data of which a reflection source is tissue inside the living body P (fundamental components). Accordingly, by extracting the harmonic components or subharmonic components from the reflected wave data of the living body P, the processing circuitry 180 can generate B mode data for generating contrast enhanced image data.

The B mode data for generating contrast enhanced image data is data in which the signal intensity of the reflected wave of which the reflection source is the contrast agent is expressed by a degree of brightness. By extracting the fundamental components from the reflected wave data of the living body P, the processing circuitry 180 can generate B mode data for generating tissue image data.

When CHI is performed, the processing circuitry 180 can extract harmonic components by a method different from the method used for filtering processing described above. In the harmonic imaging, imaging methods called an amplitude modulation (AM) method, a phase modulation (PM) method, and an AMPM method in which the AM method and the PM method are combined are performed.

In AM, PM and AMPM methods, transmission of ultrasonic waves having different amplitudes and phases is performed more than one time on the same scan line. Thus, the ultrasound reception circuitry 120 generates a plurality of pieces of reflected wave data for each scan line, and outputs the generated reflected wave data. Through the B-mode processing function 181, the processing circuitry 180 extracts harmonic components by performing addition/subtraction processing according to a modulation method on the multiple pieces of the reflected wave data of each scan line. Subsequently, the processing circuitry 180 performs the envelope detection processing and the like on the reflected wave data of the harmonic components to generate B-mode data.

The Doppler processing function 182 is a function for generating data (Doppler information) based on the Doppler effect of the moving object in the Region of Interest (ROI) in the scan area by extracting motion information through the frequency analysis on the reception signal received from the ultrasound reception circuitry 120. The generated Doppler information is stored in the raw data memory (not shown) as Doppler raw data (also referred to as Doppler data) on a two-dimensional ultrasound scanning line.

Specifically, through the Doppler processing function 182, the processing circuitry 180 estimates, as motion information of the moving object, for example, an average velocity, an average dispersion value, an average power value, etc. at sample positions, thereby generating Doppler data indicative of the estimated motion information. The moving object is, for example, a blood flow, tissue such as a cardiac wall, a contrast agent, etc. Through the Doppler processing function 182, the processing circuitry 180 according to the first embodiment estimates, as motion information of blood flow (blood flow information), an average velocity of blood flow, a dispersion value of a blood flow velocity, a power value of a blood flow signal, etc. at sample positions, thereby generating Doppler data indicative of the estimated blood flow information.

Through the Doppler processing function 182, the processing circuitry 180 can execute a color Doppler method called color flow mapping (CFM). In the CFM method, ultrasound is transmitted and received multiple times along each of a plurality of scan lines. The CFM method suppresses signals (clutter signals) resulting from any stationary tissue or slow-moving tissue by using a moving target indicator (MTI) filter with respect to data strings of the same position so that blood flow-related signals can be extracted. In the CFM method, blood flow information such as a velocity of blood flow, a dispersion of blood flow and power of blood flow is estimated based on the extracted blood flow signals. The image generating function 183 described later generates a distribution of the estimated blood flow information as, for example, two-color ultrasonic image data (color Doppler image data). In the following description, a mode of the ultrasonic diagnostic apparatus using color Doppler will be referred to as a blood flow imaging mode. In color display, a distribution of blood flow information is displayed in association with a predetermined color code, in which a gray scale is included in color display.

For the blood flow imaging mode, there are various kinds depending on desired clinical information. In general, there are a velocity display blood flow imaging mode, in which a direction of blood flow and an average velocity of blood flow can be visualized, and a power display blood flow imaging mode, in which a power of a blood flow signal can be visualized.

The velocity display blood flow imaging mode is a mode for displaying a color corresponding to a Doppler shift frequency based on the direction of blood flow and the average velocity of blood flow. For example, in the velocity display blood flow imaging mode, for a direction of flow, an oncoming flow is represented by a color near red (reddish color) while a receding flow is represented by a color near blue (bluish color), and the difference in velocity is represented by the difference in hue. The velocity display blood flow imaging mode may be called color Doppler mode or color Doppler imaging (CDI) mode.

The power display blood flow imaging mode is, for example, a mode in which power of a blood flow signal is represented by a hue near red, brightness of color, or change in chroma. The power display blood flow imaging mode may be referred to as a power Doppler (PD) mode. The power display blood flow imaging mode can extract a blood flow with a higher degree of sensitivity than the velocity display blood flow image mode and thus may be referred to as a high-sensitive blood flow imaging mode.

The image generating function 183 is a function for generating B-mode image data based on data generated through the B-mode processing function 181. For example, the processing circuitry 180 with the image generating function 183 generates image data for display (display image data) by a conversion process (scan conversion) of converting scan line signal sequences from the ultrasound scanning into scan line signal sequences in a video format as represented by televisions, etc. Specifically, the processing circuitry 180 subjects the B-mode raw data stored in the RAW data memory to raw-pixel conversion which, for example, is a coordinate conversion according to the scan configuration of the ultrasonic probe 101, to generate pixel-based two-dimensional B-mode image data (also referred to as ultrasound image data). In other words, the processing circuitry 180 with the image generating function 183 generates multiple ultrasound images (medical images) corresponding to the respective consecutive frames by utilizing ultrasound transmission and reception.

Likewise, the processing circuitry 180 subjects the Doppler raw data stored in the RAW data memory to, for example, the raw-pixel conversion to generate Doppler image data providing blood flow information in the form of images. The Doppler image data may be average velocity image data, distribution image data, power image data, or image data including any combination thereof. The processing circuitry 180 generates, as the Doppler image data, color Doppler image data showing colored blood flow information, and gray-scale Doppler image data showing single blood flow information in a wave-like gray scale. The color Doppler image data is generated at the time of executing the above-described blood flow imaging mode.

The acquiring function 184 is a function for acquiring a parameter used to determine a scanning condition of the ultrasonic diagnostic apparatus 1. For example, through the acquiring function 184, the processing circuitry 180 receives a parameter input by a user. In other words, the processing circuitry 180 acquires a parameter input by a user through the acquiring function 184. The processing circuitry 180 may acquire a changed parameter during scan execution of the ultrasonic diagnostic apparatus 1.

The first embodiment is based on the premise that the blood flow imaging mode is executed; thus, in the following description, it is assumed that the processing circuitry 180 acquires a parameter (blood flow imaging parameter) relating to a blood flow imaging mode input by a user. The blood flow imaging parameter includes at least one of information on a region of interest, information on a flow speed range, information relating to step-alternating scan, and information relating to transmit aperture synthesis. The step-alternating scan and the transmit aperture synthesis executed by the ultrasonic diagnostic apparatus 1 will be described later.

The information on a region of interest includes, for example, information on a width of the region of interest in a scan direction and a depth of the region of interest in an ultrasound radiation direction (lower end position of ROI). The width and depth of the region of interest are calculated from positional information on the region of interest with respect to an entire scan area. The entire scan area corresponds to, for example, a size of ultrasonic image that can be acquired by the ultrasonic probe 101. The information on a flow speed range includes, for example, information on an upper limit of display of an average speed of blood flow (maximum detected flow speed). The information on transmit aperture synthesis includes, for example, information on whether transmit aperture synthesis is executed. The information on step-alternating scan includes, for example, information on the ensemble number. The ensemble number will be described later.

The calculating function 185 is a function for calculating numerical information pieces for determining a scanning condition based on a parameter input by a user. The numerical information pieces include, for example, information on the number of transmit directions (the number of step-alternating transmit directions), the number of groups, and the number of compounded beams, relating to step-alternating scan. These information pieces will be described later. The processing circuitry 180 calculates, through the calculating function 185, the number of transmit directions and the number of groups relating to step-alternating scan based on the blood flow imaging parameter. Further, the processing circuitry 180 calculates, through the calculating function 185, the number of compounded beams relating to transmit aperture synthesis based on the number of groups. The processing circuitry 180 calculates (recalculates), through the calculating function 185, the number of transmit directions and the number of groups based on the number of compounded beams. The processing circuitry 180 may restrict the number of compounded beams to be calculated so that an imaging rate of a predetermined imaging mode becomes a predetermined value or more. Restricting the number of compounded beams has the same meaning as setting an upper limit to the number of compounded beams to be calculated.

The judging function 186 is a function for judging whether or not the parameter input by the user and the calculated numerical information meet a predetermined condition. Specifically, the processing circuitry 180 judges, through the judging function 186, whether or not there is an instruction for executing transmit aperture synthesis. The processing circuitry 180 judges, through the judging function 186, whether the number of compounded beams is two or more. For example, the number of compounded beams being zero means that the reception signals acquired through transmission at different times are not compounded. This is substantially similar to a case where the number of compounded beams is one. Note that "no instruction for executing transmit aperture synthesis" can be read as "instruction for not executing transmit aperture synthesis".

Further, the processing circuitry 180 may judge, through the judging function 186, whether transmit aperture synthesis is executed based on the information on the flow speed range included in the parameter. Specifically, the processing circuitry 180 judges that transmit aperture synthesis is not executed if a value of the maximum detected flow speed included in the information on the flow speed range is greater than a threshold.

The display controlling function 187 is a function for controlling the display as the output device 103 to display images based on various types of ultrasound image data generated by the image generating function 183. Specifically, for example, the processing circuitry 180 controls, through the display controlling function 187, display presentation of images which are based on the image data such as the B-mode image data and the Doppler image data generated by the image generating function 183 or the combination thereof.

More specifically, the processing circuitry 180 with the display controlling function 187 performs, for example, conversion (scan conversion) of scan line signal sequences from the ultrasound scanning into scan line signal sequences in a video format as represented by televisions or the like, to generate display image data. The processing circuitry 180 may further subject this display image data to various types of processing such as processing for the corrections of dynamic range, brightness, contrast, and a y-curve, as well as processing for RGB conversion. The processing circuitry 180 may add supplementary information, such as textual information of various parameters, a scale, or a body mark, to the image data to be displayed. The processing circuitry 180 may generate a user interface (graphical user interface: GUI) to allow an operator to input various instructions via the input device, and cause the display to display the GUI.

The processing circuitry 180 may display, through the display controlling function 187, a distribution of blood flow information on at least one of a velocity of blood flow, a dispersion of blood flow, and power of blood flow, using a blood flow signal acquired based on the scanning condition determined by the system controlling function 188 described later.

The processing circuitry 180 may display, through the display controlling function 187, information indicating that transmit aperture synthesis is being executed in the blood flow imaging mode. Specifically, the processing circuitry 180 may display a notification to a user indicating that transmit aperture synthesis is being executed.

The system controlling function 188 is a function for taking total control over the operations of the ultrasonic diagnostic apparatus 1. For example, the processing circuitry 180 with the system controlling function 188 determines a scanning condition for executing transmit aperture synthesis together with step-alternating scan based on a blood flow imaging parameter, and controls the ultrasound transmission circuitry 110 and the ultrasound reception circuitry 120 based on the scanning condition.

In the above, the basic configuration of the ultrasonic diagnostic apparatus 1 according to the first embodiment has been described. Next, transmit aperture synthesis that can be executed by the ultrasonic diagnostic apparatus 1 according to the first embodiment will be described with reference to FIGS. 13 and 14.

Figure 13:
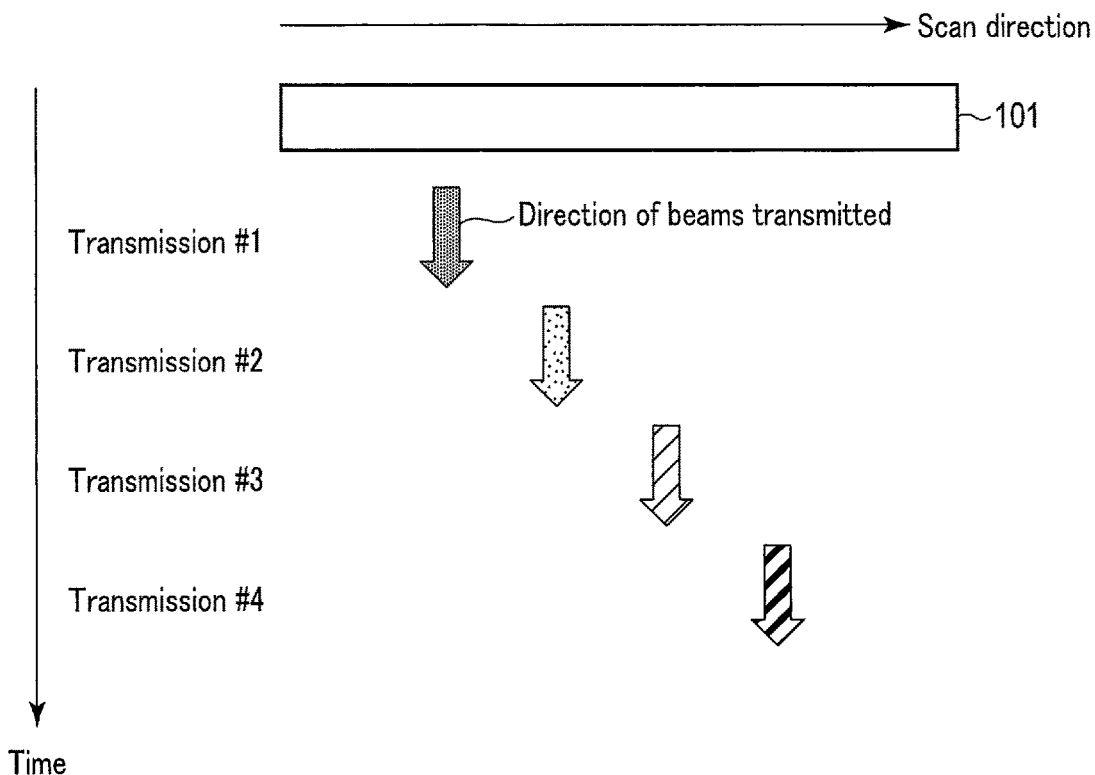
FIG. 13 is a diagram for explaining operations of transmit control through transmit aperture synthesis.

FIG. 13 is a diagram for explaining operations of transmit control through transmit aperture synthesis. The example of FIG. 13 shows a case where the ultrasonic probe 101 transmits ultrasonic waves four times in order of transmission #1, transmission #2, transmission #3, and transmission #4, by shifting the transmit focal position.

Figure 14:
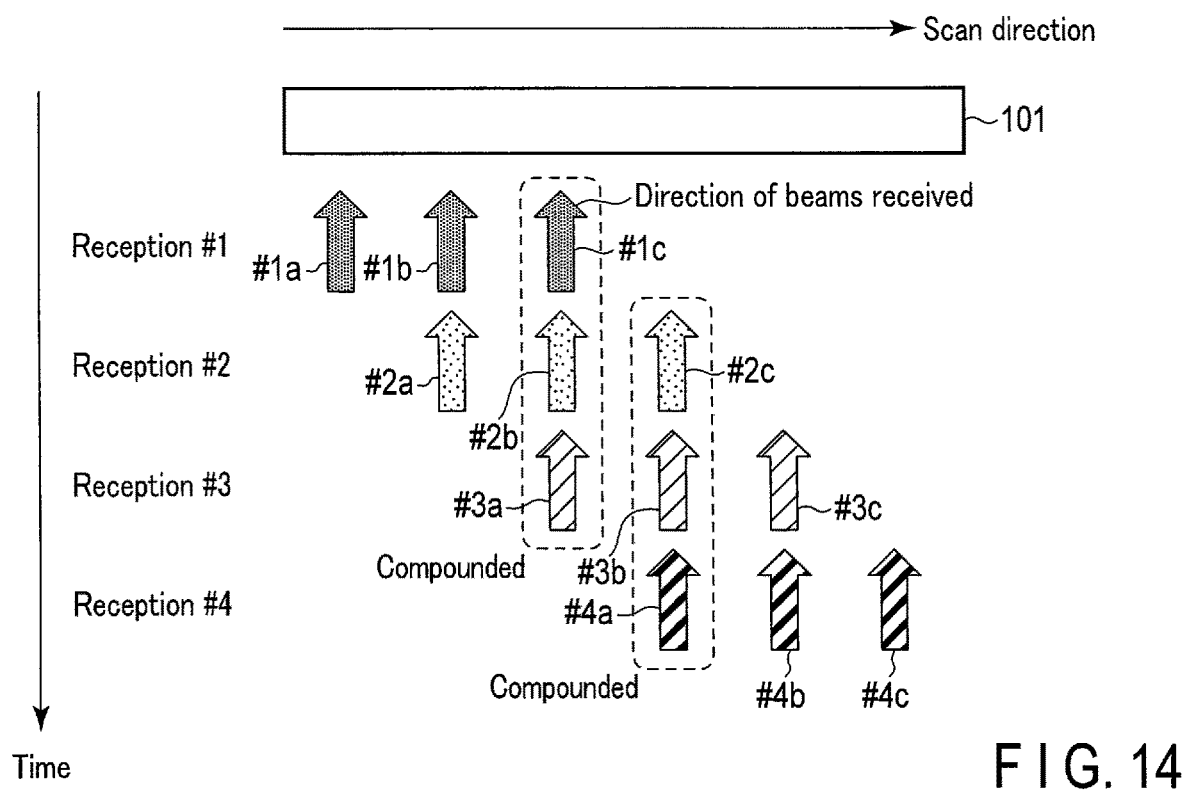
FIG. 14 is a diagram for explaining operations of receive control through transmit aperture synthesis.

FIG. 14 is a diagram for explaining operations of receive control through transmit aperture synthesis. The example of FIG. 14 shows a case where the ultrasonic probe 101 receives reflected wave signals in response to each of ultrasound transmissions of transmission #1 to transmission #4 of FIG. 13, and generates three reception signals each having different directivity. In the example of FIG. 14, the ultrasonic probe 101 receives reflected wave signals in order of reception #1, reception #2, reception #3, and reception #4, respectively corresponding to ultrasound transmissions of transmissions #1 to #4.

Specifically, at reception #1, the ultrasonic diagnostic apparatus 1 generates reception signals #1a, #1b, and #1c, in response to ultrasound transmission of transmission #1. At reception #2, the ultrasonic diagnostic apparatus 1 generates reception signals #2a, #2b, and #2c, in response to ultrasound transmission of transmission #2. Similarly, at reception #3, the ultrasonic diagnostic apparatus 1 generates reception signals #3a, #3b, and #3c, in response to ultrasound transmission of transmission #3. At reception #4, the ultrasonic diagnostic apparatus 1 generates reception signals #4a, #4b, and #4c, in response to ultrasound transmission of transmission #4.

Then, the ultrasonic diagnostic apparatus 1 compounds reception signals in the same channel obtained through different transmissions. For example, as illustrated in FIG. 14, the ultrasonic diagnostic apparatus 1 compounds the reception signals #1c, #2b, and #3a at different transmit apertures and in the same scan line. Further, for example, the ultrasonic diagnostic apparatus 1 compounds the reception signals #2c, #3b, and #4a at different transmit apertures and in the same scan line. The number of compounded beams described above corresponds to the number of compounded reception signals of the same channel obtained through different transmissions. The number of compounded beams is not limited to three as illustrated in FIG. 14, and may be two, or four or more.

Next, step-alternating scan that can be executed by the ultrasonic diagnostic apparatus 1 according to the first embodiment will be described with reference to FIG. 15 to FIG. 17.

FIG. 15 is a diagram for explaining a scan area. FIG. 15 shows an example of a region of interest R where color Doppler image data is collected by the ultrasonic probe 101. For the sake of explanation, the entire scan area will be referred to as a region of interest of a color Doppler image.

As illustrated in FIG. 15, the ultrasonic diagnostic apparatus 1 executes color Doppler mode scanning for the region of interest R to collect color Doppler image data of one frame. This region of interest R is constituted by six beams (scan lines) transmitted and received at six beam positions. Specifically, the ultrasonic diagnostic apparatus 1 divides the region of interest R into region R1 to region R6 that respectively correspond to the six beams.

Furthermore, the ultrasonic diagnostic apparatus 1 scans the region of interest R by dividing it into a plurality of groups. Specifically, the ultrasonic diagnostic apparatus 1 scans the region of interest R by dividing it into two groups of a first group of regions R1 to R3 and a second group of regions R4 to R6. Thus, each group consists of three beams.

The CFM method uses data strings of reflected wave data at the same position to generate blood flow information of one frame. Thus, the ultrasonic diagnostic apparatus 1 repeatedly executes color Doppler mode scanning for the region of interest R, thereby collecting a data string of each position (sample point) in the region of interest R. For example, the ultrasonic diagnostic apparatus 1 executes color Doppler mode scanning for the region of interest R three times at a predetermined repetition cycle, thereby collecting color Doppler image data of one frame. In the example of FIG. 15, the ultrasonic diagnostic apparatus 1 executes color Doppler mode scanning three times in each step of the divided first and second groups. In other words, the repetition cycle corresponds to the cycle of repeating color Doppler mode scanning. The number of times the color Doppler mode scanning is repeated in the group is called ensemble number Nens. The ensemble number Nens is designated by a user.

An acoustic pulse repetition frequency (PRF) corresponds to a reciprocal of duration (time) from transmission of a beam until transmission of the next beam. That is, for example, the reciprocal "f-Inv" of the acoustic PRF corresponds to a time from execution of transmission and reception of ultrasound until execution of transmission and reception of next ultrasound, and thus corresponds to transmission and reception time T1 taken for transmission and reception of each beam. The acoustic PRF is determined on the basis of, for example, at least one of a position (depth) of a lower end of region of interest R, a flow speed range, and a reception frequency of ultrasound. In other words, the ultrasonic diagnostic apparatus 1 determines the transmission and reception time T1 on the basis of at least one of a depth of the region of interest R (depth of ROI), a flow speed range, and a reception frequency of ultrasound.

Next, the ultrasonic diagnostic apparatus 1 calculates a repetition cycle T2 of the color Doppler mode scanning. The repetition cycle T2 corresponds to a duration (time) in which transmission and reception are repeatedly executed at a region. That is, the repetition cycle T2 corresponds to, for example, a time from execution of ultrasound transmission and reception at a region followed by execution of ultrasound transmission and reception at a different region until execution of ultrasound transmission and reception at the same region again, when the color Doppler mode scanning is executed multiple times in a group. The repetition cycle T2 is shorter at a higher maximum detected flow speed but longer at a lower maximum detected flow speed. Thus, the ultrasonic diagnostic apparatus 1 calculates the repetition cycle T2 on the basis of the maximum detected flow speed of the flow speed range set. The repetition cycle T2 has an identical value between regions obtained by dividing the region of interest.

Next, the ultrasonic diagnostic apparatus 1 calculates the number of directions in each step in step-alternating scan (the number of step-alternating transmit directions) Ndir, based on the repetition cycle T2 and the acoustic PRF (or transmission and reception time T1). The step-alternating scan is a method in which for collecting a data string at a predetermined region (e.g., one region) using the CFM method, instead of executing transmission and reception of ultrasound continuously for one region, a plurality of regions are combined into one group, and transmission and reception of ultrasound are executed sequentially at a plurality of regions included in the group. In FIG. 15, for example, three regions R1 to R3 are combined into one group, transmission and reception of ultrasound at the regions R1 to R3 corresponding to a first reception echo are executed sequentially, then transmission and reception of ultrasound at the regions R1 to R3 corresponding to a second reception echo are executed sequentially, and this is repeated a predetermined number of times. In this step-alternating scan, the number of regions included in each reception echo is referred to as the number of step-alternating transmit directions Ndir. That is, the number of step-alternating transmit directions Ndir corresponds to the number of regions included in each group. Next, the example of FIG. 16 shows a case where the ensemble number Nens "3" is designated by a user, and the number of step-alternating transmit directions Ndir "3" is calculated by the ultrasonic diagnostic apparatus 1.

Figure 16:
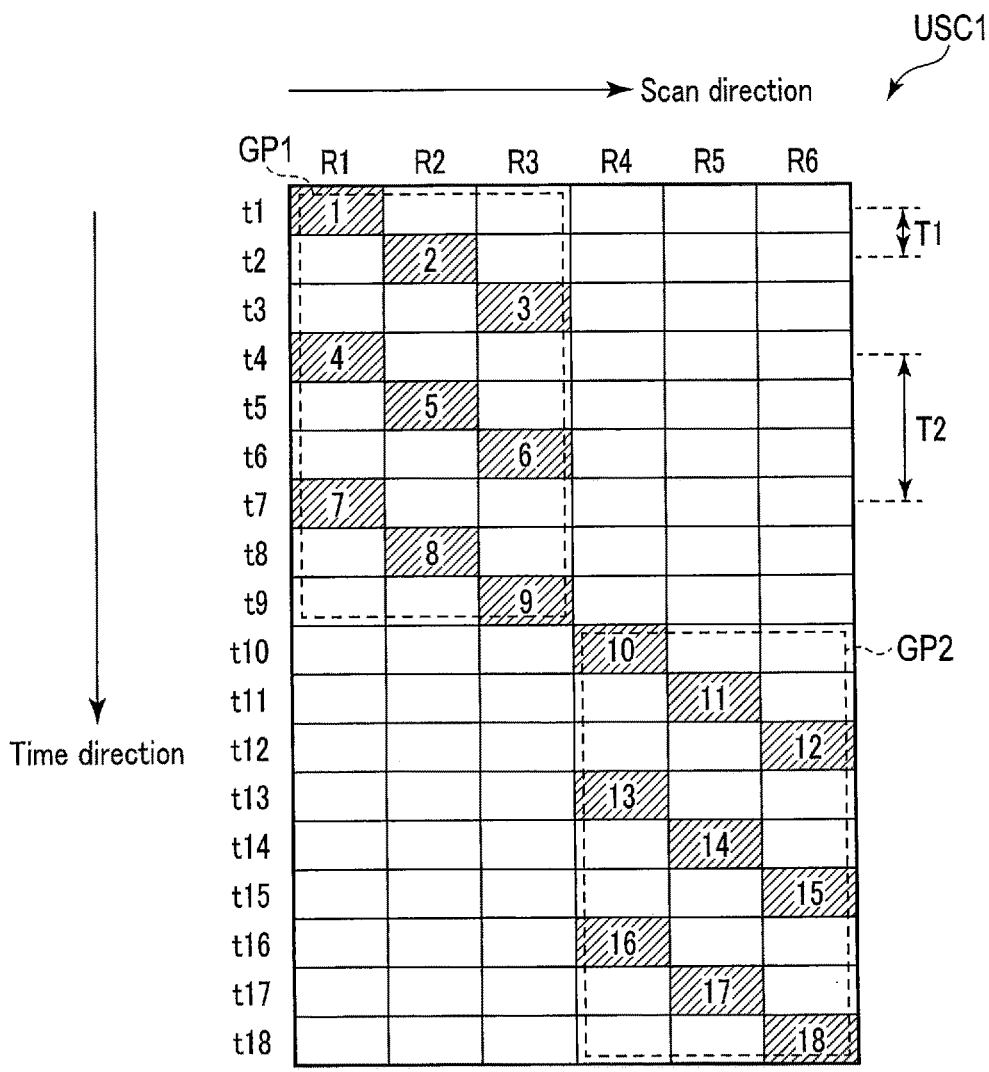
FIG. 16 is a diagram for explaining an ultrasound scanning chart.

FIG. 16 is a diagram for explaining an ultrasound scanning chart. An ultrasound scanning chart USC1 of FIG. 16 shows the order of transmission and reception of ultrasound. A lateral direction of the ultrasound scanning chart USC1 is a scan direction, and corresponds to transmission and reception of ultrasound at the regions R1 to R6 in FIG. 15. A longitudinal direction of the ultrasound scanning chart USC1 is a direction of time, and corresponds to the order of transmission and reception of ultrasound at the regions R1 to R6. The numbers in the ultrasound scanning chart USC1 correspond to the order of transmission and reception of ultrasound. For the sake of explanation, it is assumed that parallel simultaneous reception is not performed.

First, the ultrasonic diagnostic apparatus 1 executes the color Doppler mode scanning three times in each step for the first group GP1. Specifically, the ultrasonic diagnostic apparatus 1 performs ultrasound transmission and reception corresponding to the regions R1 to R3 from times t1 to t3, performs ultrasound transmission and reception corresponding to the regions R1 to R3 from times t4 to t6, and performs ultrasound transmission and reception corresponding to the regions R1 to R3 from times t7 to t9.

After executing scanning for the first group GP1, the ultrasonic diagnostic apparatus 1 executes the color Doppler mode scanning three times in each step for the second group GP2. Specifically, the ultrasonic diagnostic apparatus 1 performs ultrasound transmission and reception corresponding to the regions R4 to R6 from times t10 to t12, performs ultrasound transmission and reception corresponding to the regions R4 to R6 from times t13 to t15, and performs ultrasound transmission and reception corresponding to the regions R4 to R6 from times t16 to t18.

After executing scanning for the second group GP2, the ultrasonic diagnostic apparatus 1 executes the color Doppler mode scanning three times in each step for the first group GP1 again. Subsequently, the color Doppler mode scanning is executed alternately for the first group GP1 and the second group GP2 in a similar manner.

In FIG. 16, the transmission and reception time T1 and the repetition cycle T2 described above can be represented as follows. The transmission and reception time T1 corresponds to, for example, a time from execution of ultrasound transmission and reception in the region R1 at time t1 until execution of ultrasound transmission and reception in the region R2 at time t2. The repetition cycle T2 corresponds to a time from execution of ultrasound transmission and reception in the region R1 at time t4 until execution of ultrasound transmission and reception in the region R1 at time t7.

Figure 17:
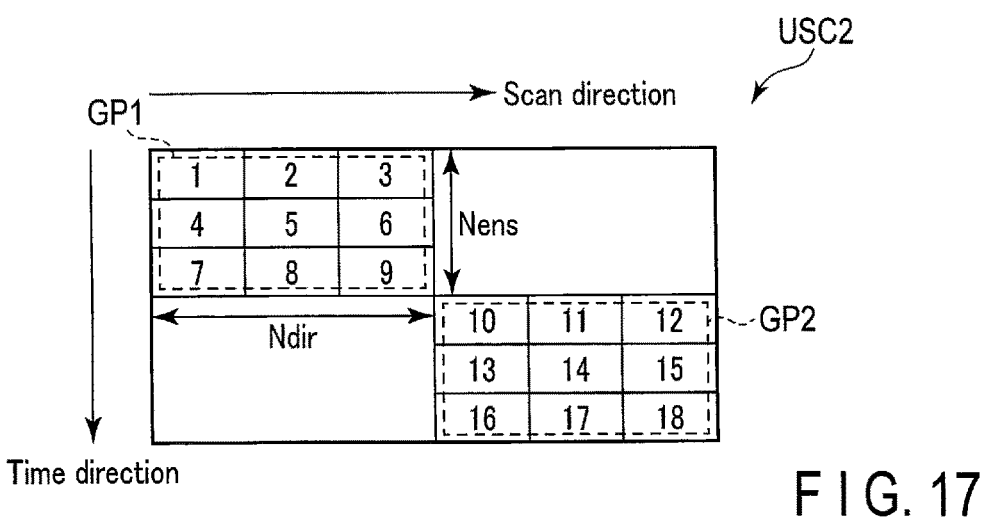
FIG. 17 is a diagram for explaining a simplified ultrasound scanning chart.

FIG. 17 is a diagram for explaining a simplified ultrasound scanning chart. An ultrasound scanning chart USC2 of FIG. 17 has contents similar to those of the ultrasound scanning chart USC1 of FIG. 16. Specifically, in the ultrasound scanning chart USC2, illustration of the direction of time of the ultrasound scanning chart USC1 is compressed. For example, in the ultrasound scanning chart USC2, the lateral direction corresponds to sets of the numbers of step-alternating transmit directions Ndir. Thus, the first row of the ultrasound scanning chart USC2 corresponds to three rows from times t1 to t3 of the ultrasound scanning chart USC1. The order of ultrasound transmission and reception illustrated with eighteen rows in the ultrasound scanning chart USC1 is illustrated with six rows in the ultrasound scanning chart USC2. In the following description, illustration of the ultrasound scanning chart USC2 will be referred to.

In the above, transmit aperture synthesis and step-alternating scan executable by the ultrasonic diagnostic apparatus 1 according to the first embodiment have been described. Next, operations of the ultrasonic diagnostic apparatus 1 according to the first embodiment will be described.

FIG. 2 is a flowchart for explaining operations of processing circuitry that executes the scanning condition determination processing in the first embodiment. The scanning condition determination processing in the first embodiment determines an optimum scanning condition when transmit aperture synthesis is executed together with step-alternating scan. The scanning condition determination processing shown in FIG. 2 is started by, for example, a user executing a discretionary blood flow imaging mode before execution of a blood flow imaging mode.

(Step ST110)

Upon start of the scanning condition determination processing, the processing circuitry 180 executes the acquiring function 184. When executing the acquiring function 184, the processing circuitry 180 receives a parameter. Specifically, the processing circuitry 180 acquires a blood flow imaging parameter input by a user. The blood flow imaging parameter is, for example, a width of a region of interest, a depth of a region of interest, a flow speed range, an ensemble number, an execution instruction for transmit aperture synthesis, etc. Next, the width and depth of the region of interest will be described with reference to FIG. 3.

FIG. 3 is a diagram for explaining an entire scan area and a region of interest in the first embodiment. FIG. 3 shows an example of a B-mode region BR as the entire scan area, and a region of interest CR where color Doppler image data is collected by the ultrasonic probe 101. A width W of the region of interest is a length of the region of interest CR in the scan direction. A depth D of the region of interest is a length from a contact surface of the ultrasonic probe 101 to a lower end of region of interest CR.

After the width W of the region of interest is set, the processing circuitry 180 divides the region of interest CR into a plurality of partial regions. The partial regions respectively correspond to, for example, elements of the ultrasonic probe 101. Therefore, the processing circuitry 180 divides the region of interest CR into partial regions based on the number of elements of the ultrasonic probe 101 corresponding to the width W of the region of interest.

Figure 4:
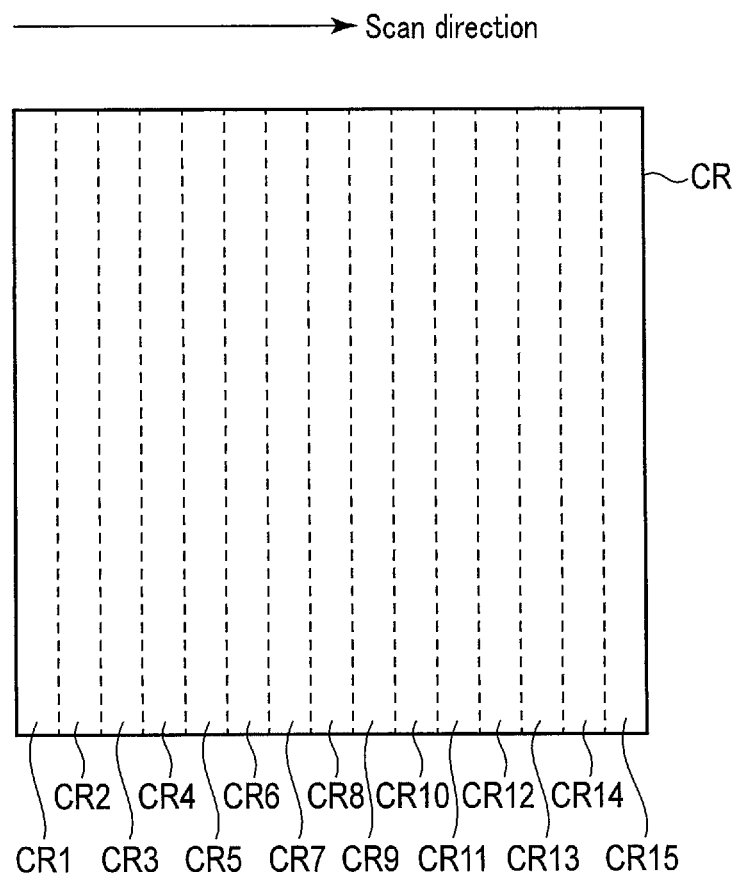
FIG. 4 is a diagram for explaining division of the region of interest in the first embodiment.

FIG. 4 is a diagram for explaining division of the region of interest in the first embodiment. FIG. 4 exemplifies the region of interest CR, and fifteen partial regions CR1 to CR15 obtained by dividing the region of interest CR in the scan direction. In the following description, a description will be given assuming that the region of interest CR is divided into the fifteen partial regions CR1 to CR15, unless the width W of the region of interest is changed. The number of divided regions in the region of interest may be paraphrased as "a dividing number of a region of interest".

(Step ST120)

After acquiring the blood flow imaging parameter, the processing circuitry 180 executes the calculating function 185. Upon execution of the calculating function 185, the processing circuitry 180 calculates the number of transmit directions and the number of groups relating to step-alternating scan based on the parameter.

Figure 5:
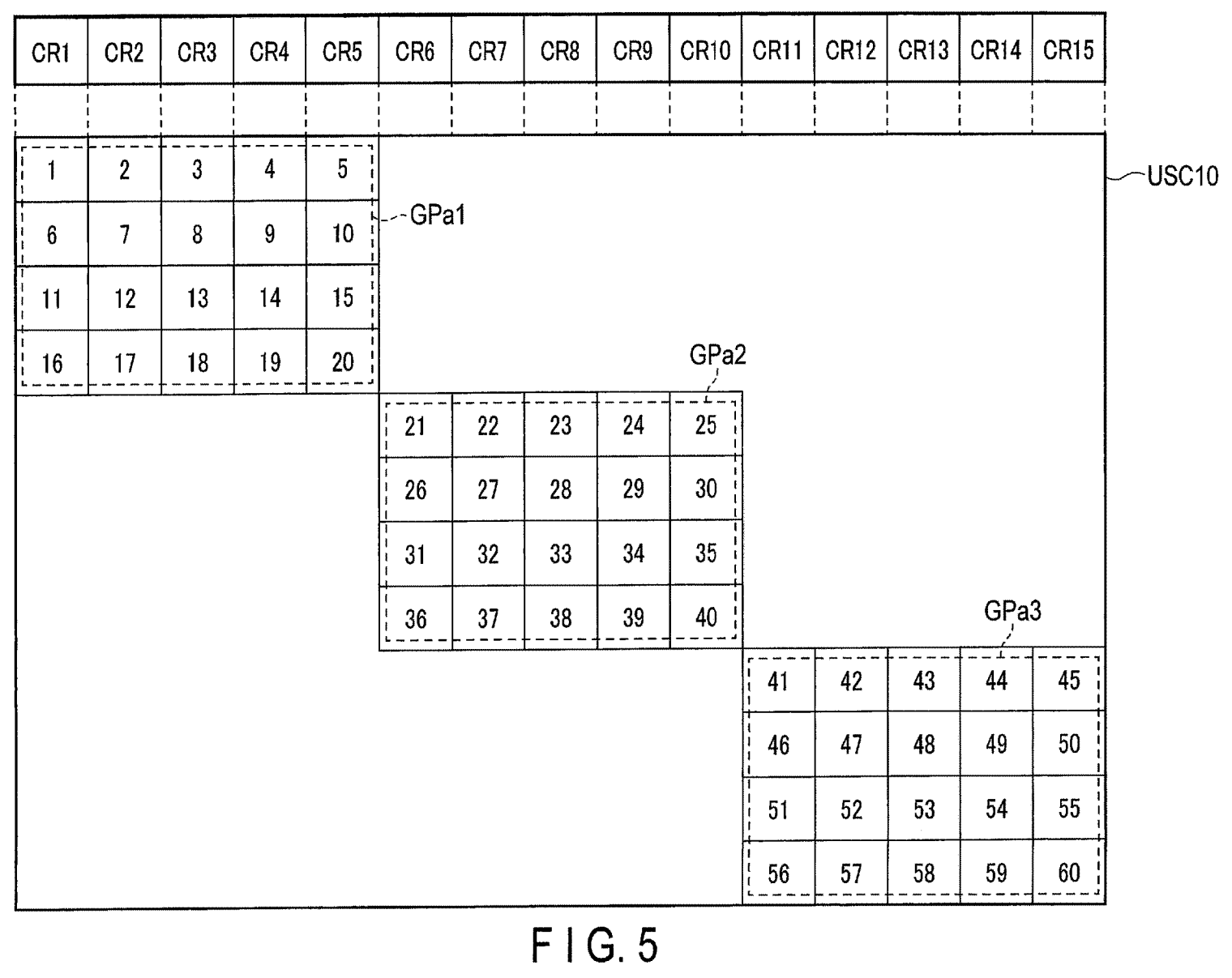

Specifically, the processing circuitry 180 calculates the transmission and reception time T1 of ultrasound scanning based on the depth of the region of interest, and calculates the repetition cycle T2 of ultrasound scanning based on the maximum detected flow speed of the flow speed range. Next, the processing circuitry 180 calculates the number of transmit directions relating to step-alternating scan based on the transmission and reception time T1 and the repetition cycle T2. The processing circuitry 180 calculates the number of groups relating to step-alternating scan based on the number of transmit directions and the dividing number of the region of interest. The ultrasound scanning chart in which, for example, the number of transmit directions "5" and the number of groups "3" are calculated according to the above calculation results will be described with reference to FIG. 5. In the example of FIG. 5, it is assumed that the ensemble number "4" is input by a user.

FIG. 5 is a diagram for explaining an ultrasound scanning chart in the first embodiment. An ultrasound scanning chart USC10 of FIG. 5 is based on the processing results through step ST120. An example in which the ultrasound scanning chart USC10 has three groups GPa1 to GPa3 is shown. The group GPa1 corresponds to five partial regions CR1 to CR5. The group GPa2 corresponds to five partial regions CR6 to CR10. The group Gpa3 corresponds to five partial regions CR11 to CR15.

A total number of ultrasound scans included in each group is 20 times, obtained from the number of transmit directions "5" and the ensemble number "4". A total number of ultrasound scans of all groups combined is 60 times. A total number of ultrasound scans of all groups combined may be paraphrased as "a total number of ultrasound scans in a region of interest".

Meanwhile, in the middle of ultrasound scanning in the region of interest, in general, an entire scan area is subject to ultrasound scanning (ultrasound scanning for acquiring B-mode image). In the following description, for the sake of explanation, it is assumed that ultrasound scanning for acquiring a B-mode image is performed at a given time interval. Therefore, the imaging rate for displaying the region of interest substantially corresponds to the total number of ultrasound scans of all groups combined.

(Step ST130)

After calculating the number of transmit directions and the number of groups, the processing circuitry 180 executes the judging function 186. Upon execution of the judging function 186, the processing circuitry 180 judges whether there is an instruction for executing transmit aperture synthesis.

Specifically, the processing circuitry 180 makes judgments based on information relating to transmit aperture synthesis of the blood flow imaging parameter. If the information relating to transmit aperture synthesis is information on executing transmit aperture synthesis, the processing circuitry 180 judges that there is an instruction for executing transmit aperture synthesis. In contrast, if the information relating to transmit aperture synthesis is information on not executing transmit aperture synthesis, the processing circuitry 180 judges that there is no instruction for executing transmit aperture synthesis.

If it is judged that there is an instruction for executing transmit aperture synthesis, the processing proceeds to step ST140. If it is judged that there is no instruction for executing transmit aperture synthesis, the processing proceeds to step ST170.

(Step ST140)

After judging that there is an instruction for executing transmit aperture synthesis, the processing circuitry 180 calculates, through the calculating function 185, the number of compounded beams relating to transmit aperture synthesis based on the number of groups.

Specifically, the processing circuitry 180 judges whether to perform transmit aperture synthesis based on the number of groups. For example, if the number of groups is three or less, the processing circuitry 180 judges that transmit aperture synthesis is performed, and calculates the number of compounded beams. If it is judged that transmit aperture synthesis is not performed, the processing circuitry 180 sets the number of compounded beams to zero.

Normally, when transmit aperture synthesis is performed, a total number of ultrasound scans in the region of interest increases as compared to when transmit aperture synthesis is not performed (details of which will be described later). Furthermore, if the width of the region of interest and the ensemble number are constant, when the transmission and reception time T1 or the repetition cycle T2 changes, the number of groups may change while the total number of ultrasound scans in the region of interest remains constant. Assuming that the total number of ultrasound scans in the region of interest is the same and the number of groups is different, a condition in which the number of groups is large increases the number of ultrasound scans when transmit aperture synthesis is performed as compared to a condition in which the number of groups is small.

Figure 6:
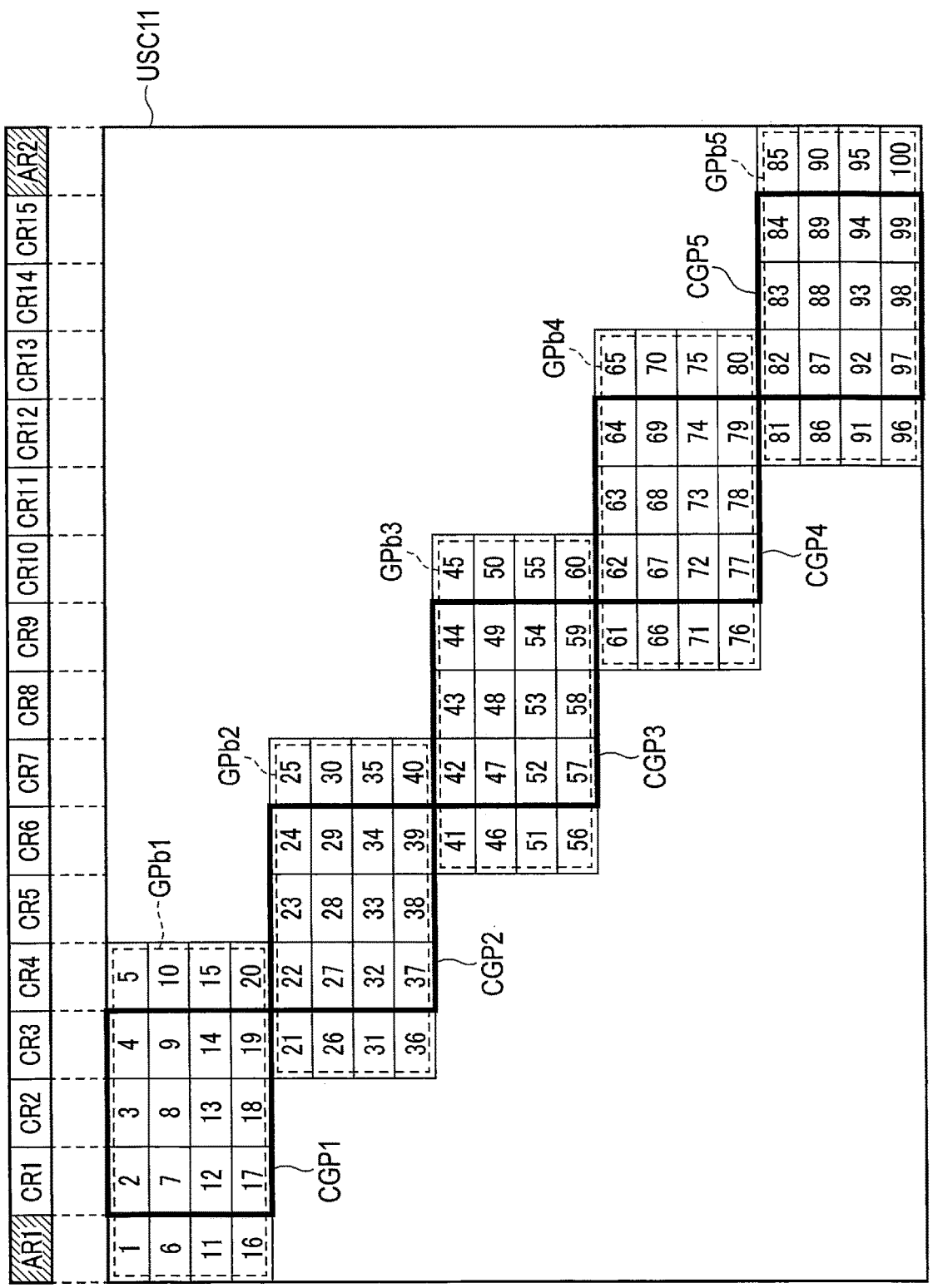
FIG. 6 is a diagram for explaining an ultrasound scanning chart when transmit aperture synthesis is executed in the first embodiment.

Specifically, as exemplified in FIG. 6, in a condition that the ultrasound scanning chart of FIG. 5 is met, when transmit aperture synthesis in which the number of compounded beams is "3" is performed, the total number of ultrasound scans in the region of interest is 100 times. On the other hand, if transmit aperture synthesis in which the number of compounded beams is "3" is performed when the number of groups is five while the total number of ultrasound scans in the region of interest is maintained to be 60 times, the total number of ultrasound scans in the region of interest is 180 times. Thus, it is effective to judge whether to perform transmit aperture synthesis based on the number of groups. The number of groups to be a threshold is set in a discretionary manner.

Next, the processing circuitry 180 calculates a total number of ultrasound scans in the region of interest when transmit aperture synthesis is performed for each of the numbers of compounded beams. The processing circuitry 180 calculates an allowable maximum number of compounded beams from multiple numbers of compounded beams based on the imaging rate for displaying the region of interest, i.e., based on an allowable total number of ultrasound scans in the region of interest. For example, the processing circuitry 180 calculates the number of compounded beams "3" assuming that an allowable total number of ultrasound scans in the region of interest is 100 times or less.

(Step ST150)

After calculating the number of compounded beams, the processing circuitry 180 judges, through the judging function 186, whether the number of compounded beams is two or more. If it is judged that the number of compounded beams is not two or more, the processing proceeds to step ST170. The number of compounded beams being not two or more is, for example, a case of the number of compounded beams being zero or one, which means that transmit aperture synthesis is not executed together with step-alternating scan based on the blood flow imaging parameter input by the user. If it is judged that the number of compounded beams is two or more, the processing proceeds to step ST160.

(Step ST160)

After it is judged that the number of compounded beams is two or more, the processing circuitry 180 calculates, through the calculating function 185, the number of second groups based on the number of compounded beams. The number of second groups is obtained in the process of calculation of the number of compounded beams in step ST140, and therefore, the value calculated in step ST140 may be set to the number of second groups.

Specifically, the processing circuitry 180 calculates the number of second groups based on the number of transmit directions, the number of compounded beams, and the number of groups or the dividing number of the region of interest. For example, the processing circuitry 180 calculates, as the number of second groups, a value obtained by dividing the diving number of the region of interest by a value obtained by adding "1" to an absolute value of the difference between the number of transmit directions and the number of compounded beams. The dividing number of the region of interest can be represented by multiplying the number of transmit directions and the number of groups. In the following description, a case where the number of second groups is "5" will be described with reference to FIG. 6. In the example of FIG. 6, it is assumed that the number of compounded beams is "3".

FIG. 6 is a diagram for explaining an ultrasound scanning chart when transmit aperture synthesis is executed in the first embodiment. An ultrasound scanning chart USC11 of FIG. 6 is based on the processing results in step ST160. An example in which the ultrasound scanning chart USC11 has five groups GPb1 to GPb5 is shown. In the ultrasound scanning chart USC11, both ends of the region of interest CR are provided with additional regions outside the region of interest. Specifically, in the ultrasound scanning chart USC11, additional region AR1 is provided to the left of the partial region CR1, and additional region AR2 is provided to the right of the partial region CR15. Next, the reason why these additional regions are provided will be described with reference to FIG. 7 and FIG. 8.

FIG. 7 is a diagram for explaining operations of transmit control through transmit aperture synthesis in the first embodiment. The example of FIG. 7 shows a case where the ultrasonic probe 101 transmits ultrasonic waves five times in order of transmission #101, transmission #102, transmission #103, transmission #104, and transmission #105, by shifting the transmit focal position. Positions of elements from which transmission is performed correspond to partial regions and additional regions. That is, the ultrasonic probe 101 performs transmission #101 to correspond to the additional region AR1, transmission #102 to correspond to the partial region CR1, transmission #103 to correspond to the partial region CR2, transmission 4104 to correspond to the partial region CR3, and transmission #105 to correspond to the partial region CR4.

Figure 8:
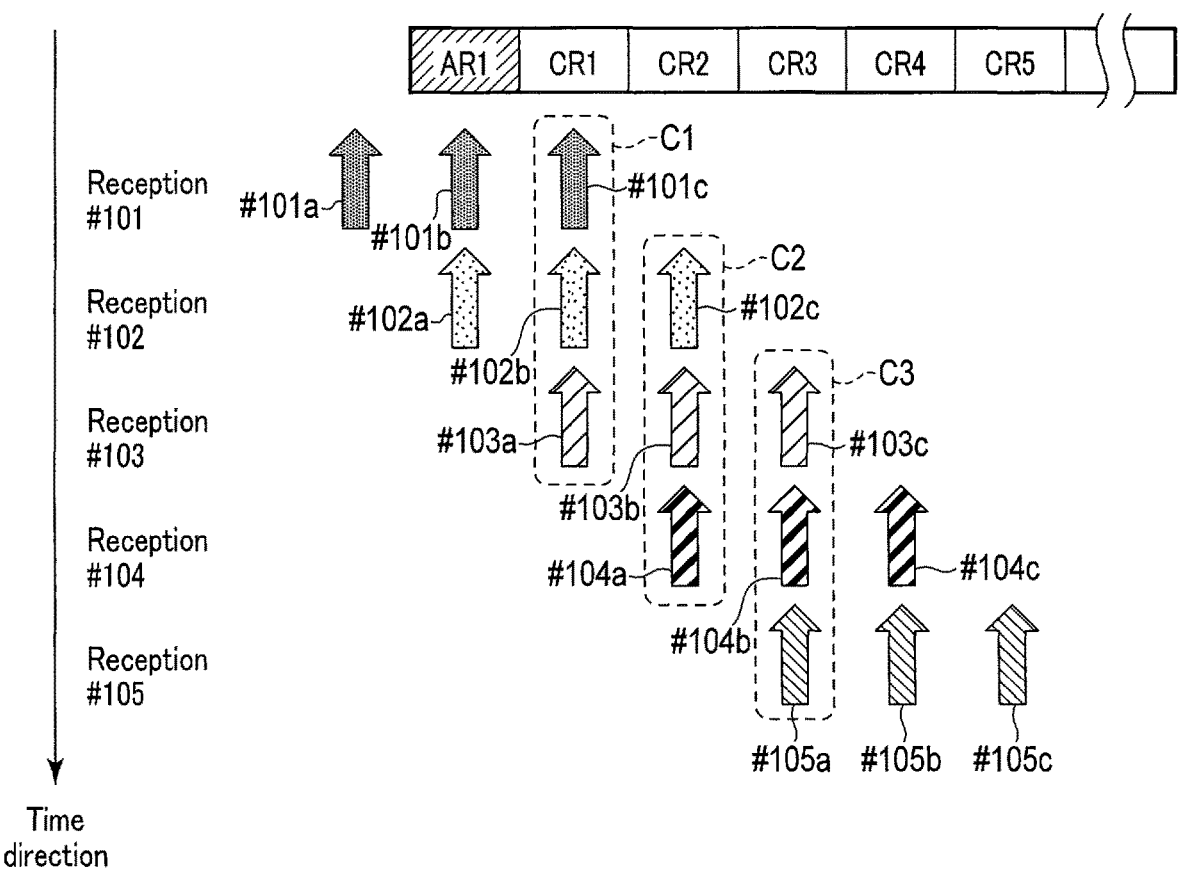
FIG. 8 is a diagram for explaining operations of receive control through transmit aperture synthesis in the first embodiment.

FIG. 8 is a diagram for explaining operations of receive control through transmit aperture synthesis in the first embodiment. The example of FIG. 8 shows a case where the ultrasonic probe receives reflected wave signals in response to each of ultrasound transmissions of transmission #101 to transmission #105 of FIG. 7, and generates three received signals each having a different reception directivity. In the example of FIG. 8, the ultrasonic probe 101 receives reflected wave signals in order of reception #101, reception #102, reception #103, reception #104, and reception #105, corresponding to respective ultrasound transmissions of transmissions #101 to #105.

Specifically, the processing circuitry 180 generates, at reception #101, reception signals #101a, #101b, and #101c, in response to ultrasound transmission of transmission #101. The processing circuitry 180 generates, at reception #102, reception signals #102a, #102b, and #102c, in response to ultrasound transmission of transmission #102. Similarly, the processing circuitry 180 generates, at reception #103, reception signals #103a, #103b, and #103c, in response to ultrasound transmission of transmission #103. The processing circuitry 180 generates, at reception #104, reception signals #104a, #104b, and #104c, in response to ultrasound transmission of transmission #104. The processing circuitry 180 generates, at reception #105, reception signals #105a, #105b, and #105c, in response to ultrasound transmission of transmission #105.

The processing circuitry 180 compounds the reception signals of the same partial region obtained through different transmissions. For example, as illustrated in FIG. 8, the processing circuitry 180 compounds the reception signals #101c, #102b, and #103a at different transmit apertures and in the partial region CR1 (Compound C1). The processing circuitry 180 compounds the receptions signals #102c, #103b, and #104a at different transmit apertures and in the partial region CR2 (Compound C2). Similarly, the processing circuitry 180 compounds the reception signals #103c, #104b, and #105a at different transmit apertures and in the partial region CR3 (Compound C3). As the number of compounded beams is "3", in the additional region AR1, only two of the reception signals #101b and #102a are obtained and the processing circuitry 180 does not perform compounding. However, since the reception signal #101c at reception #101 in response to transmission #101 corresponding to the additional region AR1 is used for Compound. C1, there is a need to provide an additional region outside the region of interest.

For the reason set forth above, in the ultrasound scanning chart USC11 of FIG. 6, additional region AR1 is provided to the left of the partial region CR1, and additional region AR2 is provided to the right of the partial region CR15. Next, regions where reception signals are compounded in each group of FIG. 6 will be described.

Group GPb1 corresponds to additional region AR1 and four partial regions CR1 to CR4. Of the group GPb1, a group corresponding to three partial regions CR1 to CR3 will be referred to as compound group CGP1. The reason why the additional region AR1 and the partial region CR4 are not included in the compound group CGP1 is as described above.

Group GPb2 corresponds to five partial regions CR3 to CR7. Of the group GPb2, a group corresponding to three partial regions CR4 to CR6 will be referred to as compound group CGP2.

At this time, the groups GPb1 and GPb2 share overlapping columns of the partial region CR3 and the partial region CR4. This results from regions where reception signals are compounded being smaller than regions where ultrasound transmit is performed. That is, in order to perform aperture synthesis for all of partial regions in the region of interest, the compound groups in the groups need to cover all the region of interest.

Similarly, group GPb3 corresponds to five partial regions CR6 to CR10. Of the group GPb3, a group corresponding to three partial regions CR7 to CR9 will be referred to as compound group CGP3. Group GPb4 corresponds to five partial regions CR9 to CR13. Of the group GPb4, a group corresponding to three partial regions CR10 to CR12 will be referred to as compound group CGP4. Group GPb5 corresponds to four partial regions CR12 to CR15 and additional region AR2. Of the group GPb5, a group corresponding to three partial regions CR13 to CR15 will be referred to as compound group CGP5. Accordingly, with the five compound groups CGP1 to CGP5, all of the fifteen partial regions CR1 to CR15 are covered.

The total number of ultrasound scans included in each group of FIG. 6 is 20 times as in FIG. 5. However, since the number of groups increases from three to five, the total number of ultrasound scans of all groups combined is 100 times.

(Step ST170)

After judging that there is no instruction for executing transmit aperture synthesis (the flow having proceeded from step ST130), or after judging that the number of compounded beams is not two or more (the flow having proceeded from step ST150), or after calculating the number of second groups (the flow having proceeded from step ST160), the processing circuitry 180 determines a scanning condition through the system controlling function 188. As a scanning condition to be determined, for example, there are two scanning conditions, i.e., a scanning condition to be determined if the flow has proceeded from step ST130 or step ST150, and a scanning condition to be determined if the flow has proceeded from step ST160.

If the flow has proceeded from step ST130 or step ST150, the processing circuitry 180 determines a scanning condition for executing only step-alternating scan based on the number of transmit directions and the number of groups calculated in step ST120.

If the flow has proceeded from step ST160, the processing circuitry 180 determines a scanning condition for executing transmit aperture synthesis together with step-alternating scan based on the number of transmit directions calculated in step ST120, the number of compounded beams calculated in step ST140, and the number of second groups calculated in step ST160. After the step ST170, the scanning condition determination processing ends.

After the processing of step ST110, it may be judged whether to execute transmit aperture synthesis based on the information on the flow speed range included in the blood flow imaging parameter. Specifically, the processing circuitry 180 judges, through the judging function 186, that transmit aperture synthesis is not executed if a value of the maximum detected flow speed included in the information on the flow speed range is greater than a threshold.

As described above, the ultrasonic diagnostic apparatus according to the first embodiment acquires a parameter relating to a predetermined imaging mode including at least information on an instruction for executing transmit aperture synthesis, and determines, based on the parameter, a scanning condition for executing transmit aperture synthesis together with step-alternating scan.

The parameter described above may further include information on a region of interest, information on a flow speed range, and information relating to step-alternating scan, and the ultrasonic diagnostic apparatus according to the first embodiment may calculate, based on the parameter, the number of transmit directions and the number of first groups relating to step-alternating scan, calculate, based on the number of the first groups, the number of compounded beams relating to transmit aperture synthesis, calculate, based on the number of compounded beams, the number of second groups, and determine a scanning condition based on the number of transmit directions, the number of second groups, and the number of compounded beams.

Therefore, the ultrasonic diagnostic apparatus according to the first embodiment can determine an optimum scanning condition for an imaging mode relating to ultrasound diagnosis.

Moreover, since the ultrasonic diagnostic apparatus according to the first embodiment can set the number of compounded beams to be zero, the maximum speed range that can be taken is the same as before, and in the speed range in which transmit aperture synthesis is possible, a displacement amount and a velocity of living tissue can be visualized from a transmission and reception acoustic field that is more uniform than before. Therefore, for the ultrasonic diagnostic apparatus according to the first embodiment, an image quality of an imaging mode relating to ultrasound diagnosis can be expected to improve.

Furthermore, the ultrasonic diagnostic apparatus according to the first embodiment can flexibly change settings relating to step-alternating scan and transmit aperture synthesis while an image quality of an imaging mode relating to ultrasound diagnosis is maintained.

(Application Example of First Embodiment)

In the first embodiment described above, the scanning condition determination processing is executed before the blood flow imaging mode is executed. On the other hand, in an application example of the first embodiment, the scanning condition determination processing is executed during execution of the blood flow imaging mode.

Figure 9:
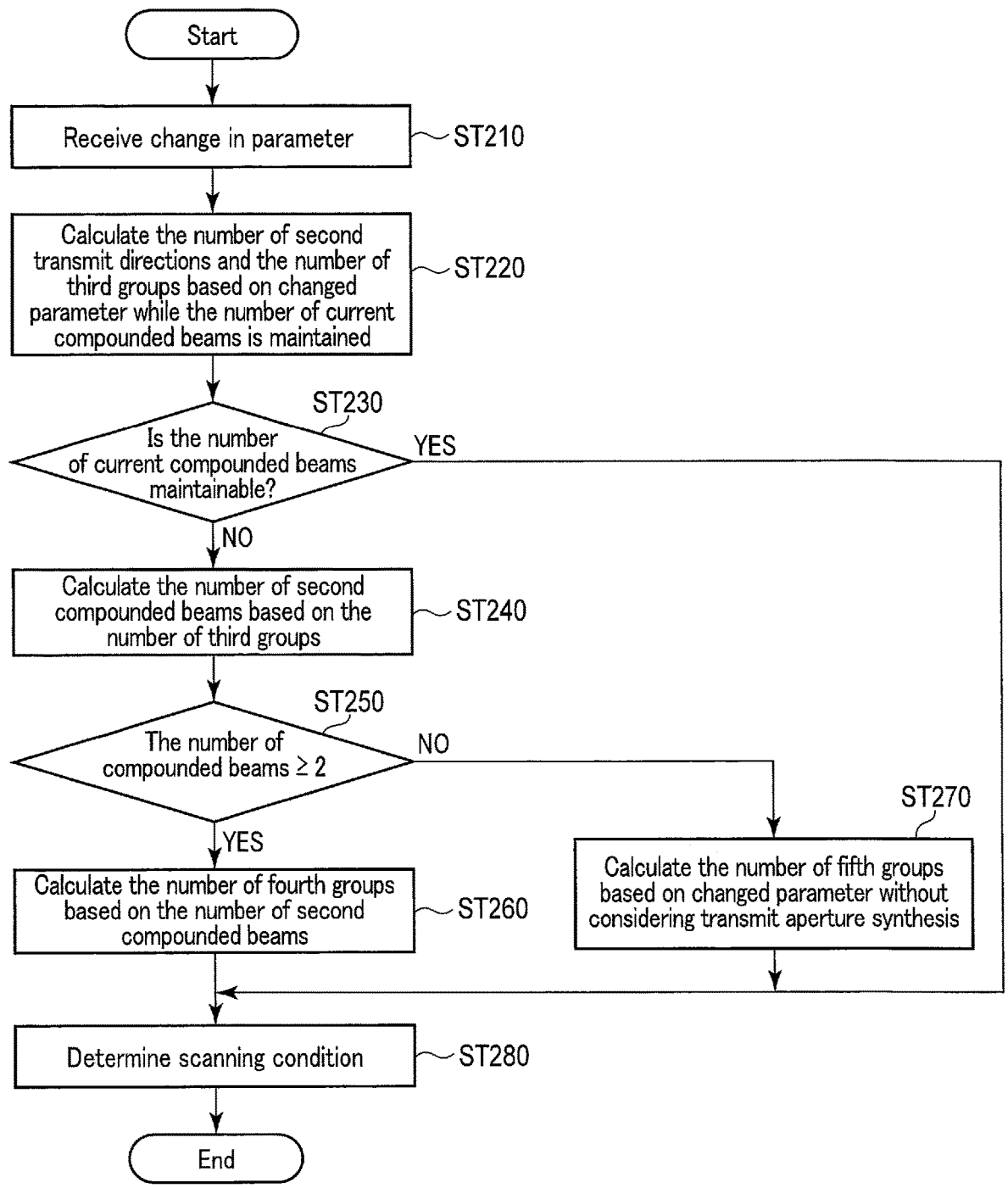
FIG. 9 is a flowchart for explaining operations of processing circuitry executing scanning condition determination processing in an application example of the first embodiment.

FIG. 9 is a flowchart for explaining operations of processing circuitry that executes scanning condition determination processing in an application example of the first embodiment. The scanning condition processing shown in FIG. 9 is started when, for example, the ultrasonic diagnostic apparatus 1 receives a parameter changed by a user during execution of the blood flow imaging mode.

For the sake of explanation, the flowchart of FIG. 9 starts in a state where the blood flow imaging mode is executed based on the scanning condition determined through the flow having proceeded from step ST160 to step ST170 in the flowchart of FIG. 2. Specifically, at the time of start of step ST210, the number of compounded beams, the number of transmit directions, and the number of second groups are already determined.

(Step ST210)

During execution of the blood flow imaging mode, the processing circuitry 180 receives, through the acquiring function 184, a changed parameter. Specifically, the processing circuitry 180 acquires a blood flow imaging parameter changed by a user. For the sake of explanation, it is assumed that the changed blood flow imaging parameter does not include information on not executing transmit aperture synthesis.

(Step ST220)

After acquiring the changed blood flow imaging parameter, the processing circuitry 180 calculates, through the calculating function 185, the number of second transmit directions and the number of third groups based on the changed parameter while the number of current compounded beams is maintained. For example, it is assumed that the number of transmit directions is changed from "5" to "3" as at least one of the transmission and reception time T1 and the repetition period T2 is changed because of change in the parameter.

(Step ST230)

After calculating the number of second transmit directions and the number of third groups, the processing circuitry 180 judges, through the judging function 186, whether the number of current compounded beams is maintainable. Specifically, the processing circuitry 180 judges whether the number of compounded beams is maintainable based on the allowable total number of ultrasound scans in the region of interest. For example, if the number of compounded beams "3" is maintained in the number of transmit directions "3", the number of groups is "15", and the total number of ultrasound scans of all groups combined is 180 times. If the allowable total number of ultrasound scans in the region of interest is 60 times, the processing circuitry 180 judges that the number of current compounded beams is not maintainable.

If it is judged that the number of current compounded beams is maintainable, the processing proceeds to step ST280. If it is judged that the number of current compounded beams is not maintainable, the processing proceeds to step ST240.

(Step ST240)

After judging that the number of current compounded beams is not maintainable, the processing circuitry 180 calculates, through the calculating function 185, the number of second compounded beams based on the number of third groups.

Specifically, the processing circuitry 180 judges whether to perform transmit aperture synthesis based on the number of third groups. For example, if the number of groups is three or less, the processing circuitry 180 judges that transmit aperture synthesis is performed, and calculates the number of second compounded beams. If it is judged that transmit aperture synthesis is not performed, the processing circuitry 180 sets the number of compounded beams to zero.

Next, the processing circuitry 180 calculates a total number of ultrasound scans in the region of interest when transmit aperture synthesis is performed for each of the numbers of compounded beams. If it is assumed that the number of compounded beams is zero, the processing circuitry 180 calculates a total number of ultrasound scans in the region of interest when transmit aperture synthesis is not performed.

(Step ST250)

After calculating the number of second compounded beams, the processing circuitry 180 judges, through the judging function 186, whether the number of second compounded beams is two or more. If it is judged that the number of second compounded beams is two or more, the processing proceeds to step ST260. If it is judged that the number of second compounded beams is not two or more, the processing proceeds to step ST270.

(Step ST260)

After judging that the number of second compounded beams is two or more, the processing circuitry 180 calculates, through the calculating function 185, the number of fourth groups based on the number of second compounded beams. Specifically, the processing circuitry 180 calculates the number of fourth groups based on the number of second transmit directions, the number of second compounded beams, and the number of third groups or the dividing number of the region of interest. After step ST260, the processing proceeds to step ST280.

(Step ST270)

Figure 10:
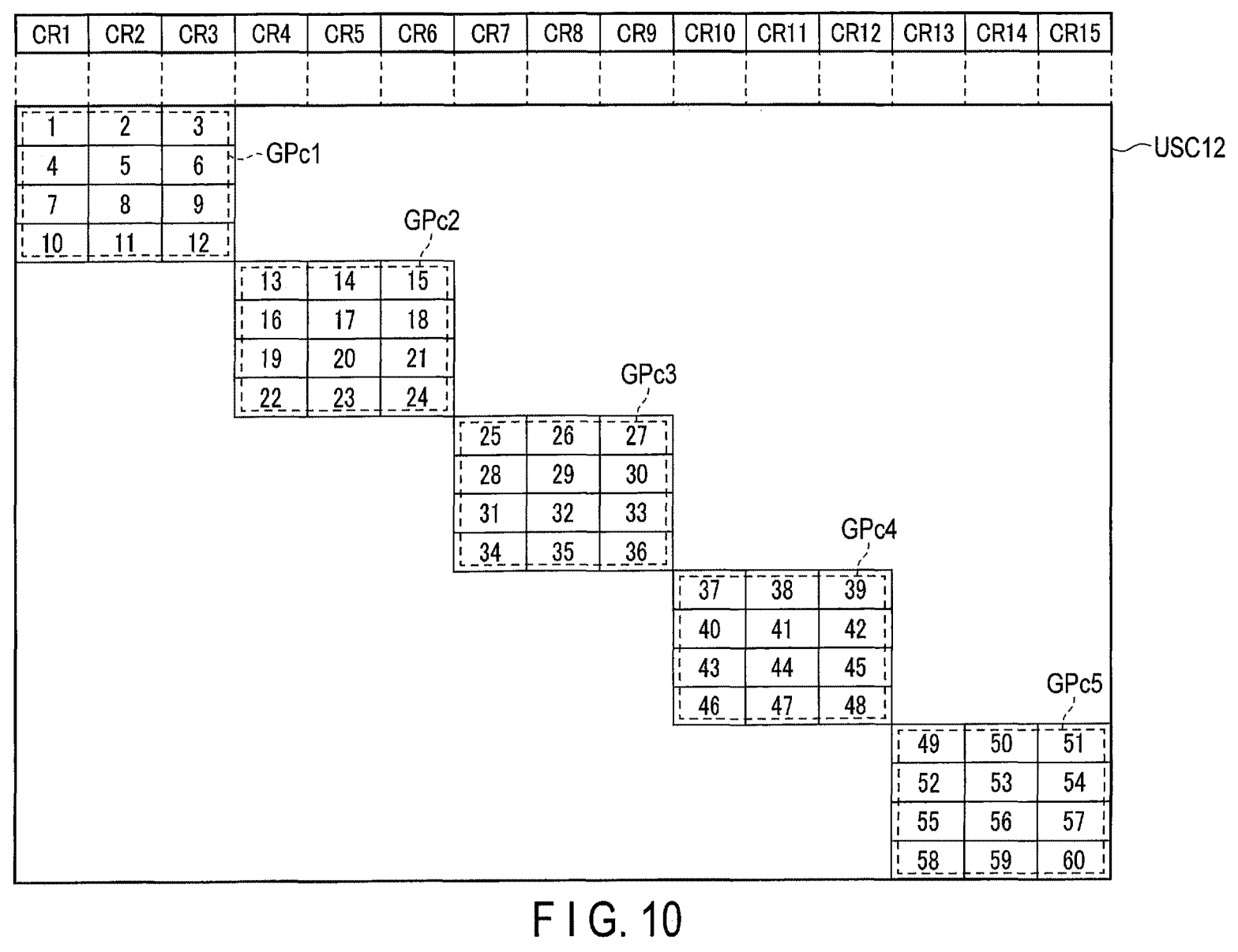

After judging that the number of second compounded beams is not two or more, the processing circuitry 180 calculates, through the calculating function 185, the number of fifth groups based on the changed parameter without considering transmit aperture synthesis. The ultrasound scanning chart in which, for example, the number of fifth groups "5" is calculated according to the calculation results will be described with reference to FIG. 10. In the example of FIG. 10, it is assumed that the number of transmit directions is "3" and the ensemble number is "4". After step ST270, the processing proceeds to step ST280.

FIG. 10 is a diagram for explaining an ultrasound scanning chart in an application example of the first embodiment. An ultrasound scanning chart USC12 of FIG. 10 is based on the processing results through step ST270. An example in which the ultrasound scanning chart USC12 has five groups GPc1 to GPc5 is shown. The group GPc1 corresponds to three partial regions CR1 to CR3. The group GPc2 corresponds to three partial regions CR4 to CR6. The group GPc3 corresponds to three partial regions CR7 to CR9. The group GPc4 corresponds to three partial regions CR10 to CR12. The group GPc5 corresponds to three partial regions CR13 to CR15.

A total number of ultrasound scans included in each group is 12 times, obtained from the number of transmit directions "3" and the ensemble number "4". A total number of ultrasound scans of all groups combined is 60 times. A total number of ultrasound scans of all groups combined in FIG. 10 is the same as the total number in FIG. 5. Thus, the imaging rate for displaying the region of interest is substantially the same in FIGS. 5 and 10.

(Step ST280)

After judging that the number of current compounded beams is maintainable (the flow having proceeded from step ST230), or after the number of fourth groups is calculated (the flow having proceeded from step ST260), or after the number of fifth groups is calculated (the flow having proceeded from step ST270), the processing circuitry 180 determines a scanning condition through the system controlling function 188. As a scanning condition to be determined, for example, there are three scanning conditions, i.e., a scanning condition to be determined if the flow has proceeded from step ST230, a scanning condition to be determined if the flow has proceeded from step ST260, and a scanning condition to be determined if the flow has proceeded from step ST270.

If the flow has proceeded from step ST230, the processing circuitry 180 determines a scanning condition for executing transmit aperture synthesis together with step-alternating scan based on the number of compounded beams determined at the time of start of step ST210, and the number of second transmit directions and the number of third groups calculated in step ST220.

If the flow has proceeded from step ST260, the processing circuitry 180 determines a scanning condition for executing transmit aperture synthesis together with step-alternating scan based on the number of second transmit directions calculated in step ST220, the number of second compounded beams calculated in step ST240, and the number of fourth groups calculated in step ST260.

If the flow has proceeded from step ST270, the processing circuitry 180 determines a scanning condition for executing only step-alternating scan based on the number of second transmit directions calculated in step ST220 and the number of fifth groups calculated in step ST270. In other words, the processing circuitry 180 determines a scanning condition not considering transmit aperture synthesis. After the step ST280, the scanning condition determination processing ends.

In step ST210, the changed blood flow imaging parameter does not include information on not executing transmit aperture synthesis, but the invention is not limited to this. For example, if the changed blood flow imaging parameter includes information on not executing transmit aperture synthesis, the processing may proceed to step ST270 assuming that transmit aperture synthesis is not executed thereafter.

As described above, the ultrasonic diagnostic apparatus according to the application example of the first embodiment may acquire a changed parameter and calculate the number of transmit directions and the number of groups based on the changed parameter while the number of compounded beams is maintained or by changing the number of compounded beams.

Therefore, the ultrasonic diagnostic apparatus according to the application example of the first embodiment can determine an optimum scanning condition even when transmit aperture synthesis is executed together with step-alternating scan.

Second Embodiment

In the first embodiment, after receipt of the parameter from the user, the number of transmit directions and the number of groups are calculated considering only step-alternating scan. On the other hand, in the second embodiment, after receipt of the parameter from the user, the number of transmit directions and the number of groups are not calculated considering only step-alternating scan.

Figure 11:
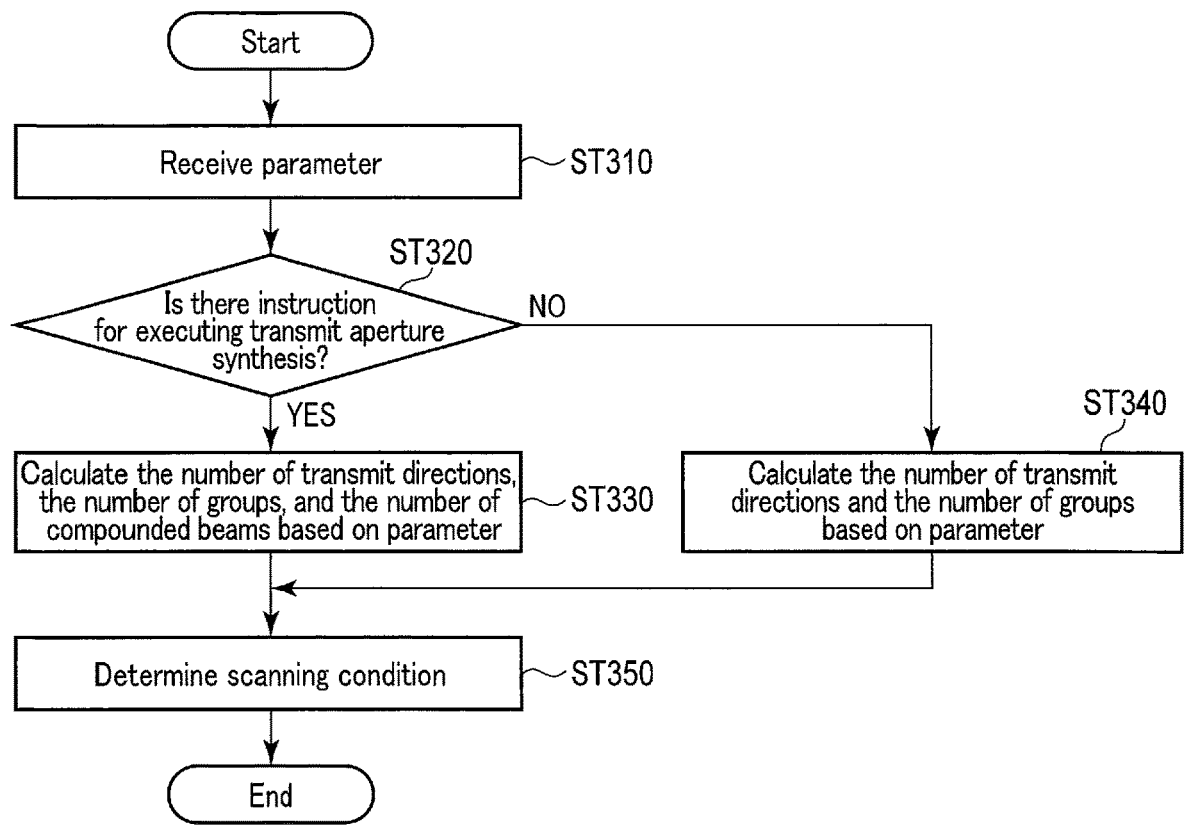
FIG. 11 is a flowchart for explaining operations of processing circuitry executing scanning condition determination processing in a second embodiment.

FIG. 11 is a flowchart for explaining operations of processing circuitry that executes scanning condition determination processing in the second embodiment. The scanning condition determination processing in the second embodiment determines an optimum scanning condition when transmit aperture synthesis is executed together with step-alternating scan. The scanning condition determination processing shown in FIG. 11 is started by, for example, a user executing a discretionary blood flow imaging mode before execution of a blood flow imaging mode.

(Step ST310)

Upon start of the scanning condition determination processing, the processing circuitry 180 receives a parameter input by a user through the acquiring function 184. Specifically, the processing circuitry 180 acquires a blood flow imaging parameter input by a user.

(Step ST320)

After acquiring the blood flow imaging parameter, the processing circuitry 180 judges, through the judging function 186, whether or not there is an instruction for executing transmit aperture synthesis. If it is judged that there is an instruction for executing the transmit aperture synthesis, the processing proceeds to step ST330. If it is judged that there is no instruction for executing the transmit aperture synthesis, the processing proceeds to step ST340. If there is an "instruction for not executing transmit aperture synthesis", it may be judged that there is no instruction for executing transmit aperture synthesis.

(Step ST330)

After judging that there is an instruction for executing the transmit aperture synthesis, the processing circuitry 180 calculates, through the calculating function 185, the number of transmit directions, the number of groups, and the number of compounded beams based on the parameter. By way of example, the processing circuitry 180 calculates the number of compounded beams based on information on a flow speed range included in the parameter. After step ST330, the processing proceeds to step ST350.

(Step ST340)

After judging that there is no instruction for executing transmit aperture synthesis, the processing circuitry 180 calculates, through the calculating function 185, the number of transmit directions and the number of groups based on the parameter. After step ST340, the processing proceeds to step ST350.

(Step ST350)

After calculating the number of transmit directions, the number of groups, and the number of compounded beams (the flow having proceeded from step ST330), or after calculating the number of transmit directions and the number of groups (the flow having proceeded from step ST340), the processing circuitry 180 determines a scanning condition through the system controlling function 188. As a scanning condition to be determined, for example, there are two scanning conditions, i.e., a scanning condition to be determined if the flow has proceeded from step ST330, and a scanning condition to be determined if the flow has proceeded from step ST340.

If the flow has proceeded from step ST330, the processing circuitry 180 determines a scanning condition for executing transmit aperture synthesis together with step-alternating scan based on the number of transmit directions, the number of groups, and the number of compounded beams calculated in step ST330. When the number of compounded beams is zero or one, the processing circuitry 180 determines a scanning condition for executing only step-alternating scan.

If the flow has proceeded from step ST340, the processing circuitry 180 determines a scanning condition for executing only step-alternating scan based on the number of transmit directions and the number of groups calculated in step ST340. After the step ST340, the scanning condition determination processing ends.

As described above, the ultrasonic diagnostic apparatus according to the second embodiment acquires a parameter relating to a predetermined imaging mode including at least information on an instruction for executing transmit aperture synthesis, and determines, based on the parameter, a scanning condition for executing transmit aperture synthesis together with step-alternating scan. The ultrasonic diagnostic apparatus according to the second embodiment may acquire a changed parameter and calculate the number of transmit directions and the number of groups based on the changed parameter while the number of compounded beams is maintained or by changing the number of compounded beams.

The parameter described above may further include information on a region of interest, information on a flow speed range, and information relating to step-alternating scan, and the ultrasonic diagnostic apparatus according to the second embodiment may calculate, based on the parameter, the number of transmit directions and the number of groups relating to step-alternating scan and the number of compounded beams relating to transmit aperture synthesis, and determine a scanning condition based on the number of transmit directions, the number of groups, and the number of compounded beams.

Therefore, the ultrasonic diagnostic apparatus according to the second embodiment can determine an optimum scanning condition for an imaging mode relating to ultrasound diagnosis.

Moreover, since the ultrasonic diagnostic apparatus according to the second embodiment can set the number of compounded beams to be zero, the maximum speed range that can be taken is the same as before, and in the speed range in which transmit aperture synthesis is possible, a displacement amount and a velocity of living tissue can be visualized from a transmission and reception acoustic field that is more uniform than before. Therefore, for the ultrasonic diagnostic apparatus according to the second embodiment, an image quality of an imaging mode relating to ultrasound diagnosis can be expected to improve.

(Application Example of Second Embodiment)

In the second embodiment described above, the scanning condition determination processing is executed before the blood flow imaging mode is executed. On the other hand, in an application example of the second embodiment, the scanning condition determination processing is executed during execution of the blood flow imaging mode.

Figure 12:
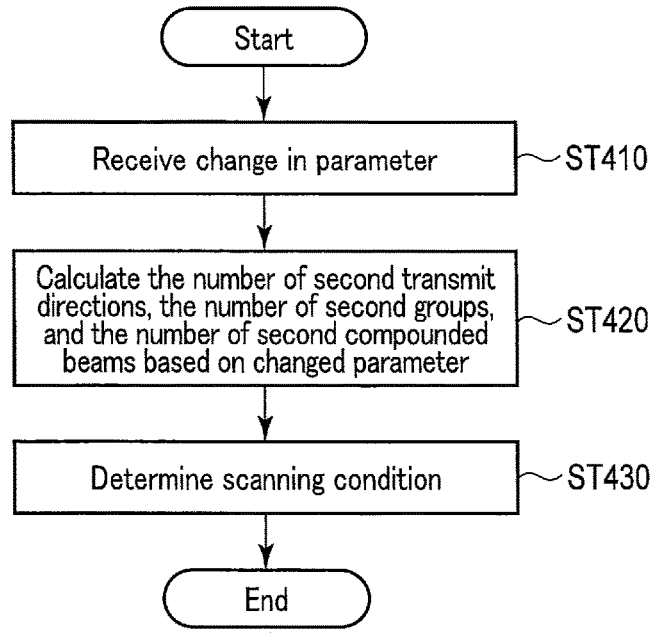
FIG. 12 is a diagram for explaining an ultrasound scanning chart in an application example of the second embodiment.

FIG. 12 is a diagram for explaining an ultrasound scanning chart in an application example of the second embodiment. The scanning condition processing shown in FIG. 12 is started when, for example, the ultrasonic diagnostic apparatus 1 receives a parameter changed by a user during execution of the blood flow imaging mode.

For the sake of explanation, the flowchart of FIG. 12 starts in a state where the blood flow imaging mode is executed based on the scanning condition determined through the flow having proceeded from step ST330 to step ST350 in the flowchart of FIG. 11. Specifically, at the time of start of step ST410, the number of compounded beams, the number of transmit directions, and the number of groups are already determined.

(Step ST410)

During execution of the blood flow imaging mode, the processing circuitry 180 receives, through the acquiring function 184, a changed parameter. Specifically, the processing circuitry 180 acquires a blood flow imaging parameter changed by a user. For the sake of explanation, it is assumed that the changed blood flow imaging parameter does not include information on not executing transmit aperture synthesis.

(Step ST420)

After acquiring the changed blood flow imaging parameter, the processing circuitry 180 calculates, through the calculating function 185, the number of second transmit directions, the number of second groups, and the number of second compounded beams based on the changed parameter. By way of example, the changed parameter includes information on a flow speed range, and the processing circuitry 180 calculates the number of second compounded beams based on information on the changed flow speed range.

(Step ST430)

After calculating the number of second transmit directions, the number of second groups, and the number of second compounded beams, the processing circuitry 180 determines a scanning condition for executing transmit aperture synthesis together with step-alternating scan based on the number of second transmit directions, the number of second groups, and the number of second compounded beams. When the number of compounded beams is zero or one, the processing circuitry 180 determines a scanning condition for executing only step-alternating scan.

As described above, the ultrasonic diagnostic apparatus according to the application example of the second embodiment may acquire a changed parameter and calculate the number of transmit directions, the number of groups, and the number of compounded beams based on the changed parameter.

Therefore, the ultrasonic diagnostic apparatus according to the application example of the second embodiment can determine an optimum scanning condition even when transmit aperture synthesis is executed together with step-alternating scan.

Another Embodiment

In each of the embodiments and each of the application examples described above, the scanning condition determination processing is executed in the blood flow imaging mode. However, the scanning condition determination processing may be used in a mode other than the blood flow imaging mode. For example, an ultrasonic diagnostic apparatus according to another embodiment executes scanning condition determination processing in a mode executed by Shear Wave Elastography (SWE) (SWE mode).

The SWE mode is a mode in which a shear wave is generated in a living body to measure a propagation velocity of the generated shear wave, thereby acquiring information on hardness of tissue.

The scanning condition determination processing described in each of the embodiments and each of the application examples described above can also be applied to the SWE mode.

The ultrasonic diagnostic apparatus according to another embodiment may display a distribution of a viscosity parameter of tissue using information on hardness of tissue acquired through the scanning condition in the SWE mode.

Therefore, the ultrasonic diagnostic apparatus according to another embodiment is expected to provide effects similar to those described in each of the embodiments described above even when SWE mode is used.

According to at least one of the above-described embodiments, it is possible to determine an optimum scanning condition of an imaging mode relating to ultrasound diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the foregoing embodiments, t1he following matters are disclosed as one aspect and a selective feature of the present invention.

(1) An ultrasonic diagnostic apparatus, comprises processing circuitry configured to:
acquire a parameter relating to a predetermined imaging mode, the parameter including at least information on an instruction for executing transmit aperture synthesis; and
determine a scanning condition for executing the transmit aperture synthesis together with step-alternating scan based on the parameter.

(2) The parameter may further include at least one of information on a region of interest, information on a flow speed range, and information on step-alternating scan, and the processing circuitry may
calculate, based on the parameter, a number of transmit directions and a number of groups relating to the step-alternating scan, and a number of compounded beams relating to the transmit aperture synthesis; and
determine the scanning condition based on the number of transmit directions, the number of groups, and the number of compounded beams.

(3) The parameter may include the information on the flow speed range, and the processing circuitry may calculate the number of compounded beams based on the information on the flow speed range.

(4) The processing circuitry may
acquire a changed parameter;
calculate a number of second transmit directions, number of second groups, and a number of second compounded beams, based on the changed parameter; and
determine the scanning condition based on the number of second transmit directions, the number of second groups, and the number of second compounded beams.

(5) The changed parameter may include information on a changed flow speed range, and the processing circuitry may calculate the number of second compounded beams based on the information on the changed flow speed range.

(6) The processing circuitry may
calculate a number of compounded beams based on a number of first groups corresponding to the number of groups;
calculate a number of second groups based on the number of compounded beams; and
determine the scanning condition based on the number of transmit directions, the number of second groups, and the number of compounded beams.

(7) The processing circuitry may
acquire a changed parameter; and
calculate a number of second transmit directions and a number of third groups based on the changed parameter while the number of compounded beams is maintained.

(8) The processing circuitry may
judge whether the number of compounded beams is maintainable; and
determine, if it is judged that the number of compounded beams is maintainable, the scanning condition based on the number of second transmit directions, the number of third groups, and the number of compounded beams.

(9) If it is judged that the number of compounded beams is not maintainable, the processing circuitry may
calculate, based on the number of third groups, a number of second compounded beams;
calculate a number of fourth groups based on the number of second compounded beams; and
determine the scanning condition based on the number of second transmit directions, the number of fourth groups, and the number of second compounded beams.

(10) The processing circuitry may restrict the number of compounded beams so that an imaging rate of the predetermined imaging mode is a predetermined value or more.

(11) The processing circuitry may restrict the number of compounded beams and the number of second compounded beams so that an imaging rate of the predetermined imaging mode is a predetermined value or more.

(12) The information on step-alternating scan may include an ensemble number that is a number of times scanning is repeated in a group in the step-alternating scan.

(13) The changed parameter may include information on not executing the transmit aperture synthesis, and the processing circuitry may determine a scanning condition not considering the transmit aperture synthesis.

(14) The parameter may include the information on the flow speed range, and the processing circuitry may judge whether the transmit aperture synthesis is executed based on the information on the flow speed range.

(15) The processing circuitry may judge that the transmit aperture synthesis is not executed if a value of a maximum detected flow speed included in the information on the flow speed range is greater than a threshold.

(16) The predetermined imaging mode is a blood flow imaging mode that displays a blood flow signal acquired by an ultrasonic probe, and the processing circuitry may display a distribution of blood flow information on at least one of a blood flow speed, a blood flow dispersion, and a blood flow power, using the blood flow signal acquired through the scanning condition.

(17) The predetermined imaging mode is a shear wave elastography (SWE) mode that acquires information on hardness of tissue by generating a shear wave in a living body and measuring a propagation speed of the generated shear wave, and the processing circuitry may display a distribution of a viscosity parameter of the tissue using the information on hardness of tissue acquired through the scanning condition.

(18) A method of determining a scanning condition, comprising:
acquiring a parameter relating to a predetermined imaging mode, the parameter including at least information on an instruction for executing transmit aperture synthesis; and
determining a scanning condition for executing the transmit aperture synthesis together with step-alternating scan, based on the parameter.

The invention claimed is:

1. A method of determining a scanning condition, comprising:
acquiring a parameter relating to a predetermined imaging mode, the parameter including at least information on an instruction for executing transmit aperture synthesis, wherein the information on the instruction for executing the transmit aperture synthesis comprises at least one of information on a region of interest, information on a flow speed range, or information on a step-alternating scan;
calculating, based on the acquired parameter, a number of transmit directions and a number of groups relating to the step-alternating scan, and a number of compounded beams relating to the transmit aperture synthesis, wherein the number of the compounded beams is calculated based on a number of first groups corresponding to the number of the groups;
calculating a number of second groups based on the number of the compounded beams;
determining the scanning condition for executing the transmit aperture synthesis together with the step-alternating scan based on the number of the transmit directions, the number of the second groups, and the number of the compounded beams; and
performing an ultrasound scan of an object based on the determined scanning condition.

2. An ultrasonic diagnostic apparatus, comprising:
processing circuitry configured to:
acquire a parameter relating to a predetermined imaging mode, the parameter including at least information on an instruction for executing transmit aperture synthesis, wherein the information on the instruction for executing the transmit aperture synthesis comprises at least one of information on a region of interest, information on a flow speed range, and information on a step-alternating scan;
calculate, based on the acquired parameter, a number of transmit directions and a number of groups relating to the step-alternating scan, and a number of compounded beams relating to the transmit aperture synthesis, wherein the number of the compounded beams is calculated based on a number of first groups corresponding to the number of the groups;
calculate a number of second groups based on the number of the compounded beams;
determine a scanning condition for executing the transmit aperture synthesis together with the step-alternating scan based on the number of the transmit directions, the number of the second groups, and the number of the compounded beams; and
perform an ultrasound scan of an object based on the determined scanning condition.

3. The ultrasonic diagnostic apparatus according to claim 2, wherein the parameter includes the information on the flow speed range, and
the processing circuitry is further configured to calculate the number of the compounded beams based on the information on the flow speed range.

4. The ultrasonic diagnostic apparatus according to claim 2, wherein the processing circuitry is further configured to:
acquire a changed parameter;
calculate a number of second transmit directions, a number of second groups, and a number of second compounded beams, based on the changed parameter; and
determine the scanning condition based on the number of the second transmit directions, the number of the second groups, and the number of the second compounded beams.

5. The ultrasonic diagnostic apparatus according to claim 4, wherein the changed parameter includes information on a changed flow speed range, and
the processing circuitry is further configured to calculate the number of the second compounded beams based on the information on the changed flow speed range.

6. The ultrasonic diagnostic apparatus according to claim 4, wherein the processing circuitry is further configured to restrict the number of the compounded beams and the number of the second compounded beams so that an imaging rate of the predetermined imaging mode is a predetermined value or more.

7. The ultrasonic diagnostic apparatus according to claim 4, wherein the changed parameter includes information indicating that the transmit aperture synthesis should not be executed, and
the processing circuitry is further configured to determine a different scanning condition without considering the transmit aperture synthesis.

8. The ultrasonic diagnostic apparatus according to claim 2, wherein the processing circuitry is further configured to:
acquire a changed parameter; and
calculate a number of second transmit directions and a number of third groups based on the changed parameter while the number of the compounded beams is maintained.

9. The ultrasonic diagnostic apparatus according to claim 8, wherein the processing circuitry is further configured to:
judge whether the number of the compounded beams is maintainable; and
determine, when it is judged that the number of the compounded beams is maintainable, the scanning condition based on the number of the second transmit directions, the number of the third groups, and the number of the compounded beams.

10. The ultrasonic diagnostic apparatus according to claim 9, wherein the processing circuitry is further configured to:
when it is judged that the number of the compounded beams is not maintainable,
calculate, based on the number of the third groups, a number of second compounded beams;
calculate a number of fourth groups based on the number of the second compounded beams; and
determine the scanning condition based on the number of the second transmit directions, the number of the fourth groups, and the number of the second compounded beams.

11. The ultrasonic diagnostic apparatus according to claim 2, wherein the processing circuitry is further configured to restrict the number of the compounded beams so that an imaging rate of the predetermined imaging mode is a predetermined value or more.

12. The ultrasonic diagnostic apparatus according to claim 2, wherein the information on the step-alternating scan includes an ensemble number that is a number of times scanning is repeated in a group in the step-alternating scan.

13. The ultrasonic diagnostic apparatus according to claim 2, wherein the parameter includes the information on the flow speed range, and
the processing circuitry is further configured to judge whether the transmit aperture synthesis is executed based on the information on the flow speed range.

14. The ultrasonic diagnostic apparatus according to claim 13, wherein the processing circuitry is further configured to judge that the transmit aperture synthesis should not be executed when a value of a maximum detected flow speed included in the information on the flow speed range is greater than a threshold.

15. The ultrasonic diagnostic apparatus according to claim 2, wherein the predetermined imaging mode is a blood flow imaging mode that displays a blood flow signal acquired by an ultrasonic probe, and
the processing circuitry is further configured to display a distribution of blood flow information on at least one of a blood flow speed, a blood flow dispersion, or a blood flow power, using the blood flow signal acquired through the scanning condition.

16. The ultrasonic diagnostic apparatus according to claim 2, wherein the predetermined imaging mode is a shear wave elastography (SWE) mode that acquires information on hardness of a tissue by generating a shear wave in a living body and measuring a propagation speed of the generated shear wave, and
the processing circuitry is further configured to display a distribution of a viscosity parameter of the tissue using the information on the hardness of the tissue acquired through the scanning condition.

17. The ultrasonic diagnostic apparatus according to claim 2, wherein the processing circuitry is further configured to:
determine whether or not the number of the compounded beams is equal to or greater than two; and
when the number of the compounded beams is equal to or greater than two, determine the scanning condition.

* * * * *